(12) United States Patent
Small et al.

(10) Patent No.: US 11,573,217 B2
(45) Date of Patent: Feb. 7, 2023

(54) LOW POWER SENSOR FOR $NO_x$ DETECTION

(71) Applicant: National Technology & Engineering Solutions of Sandia, LLC, Albuquerque, NM (US)

(72) Inventors: Leo J. Small, Albuquerque, NM (US); Susan Elizabeth Henkelis, Albuquerque, NM (US); Stephen J. Percival, Albuquerque, NM (US); Tina M. Nenoff, Albuquerque, NM (US); Mara Elizabeth Schindelholz, Columbus, OH (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 172 days.

(21) Appl. No.: 17/173,333

(22) Filed: Feb. 11, 2021

(65) Prior Publication Data
US 2022/0260541 A1    Aug. 18, 2022

(51) Int. Cl.
*G01N 33/00*    (2006.01)
*G01N 27/22*    (2006.01)

(52) U.S. Cl.
CPC ....... *G01N 33/0037* (2013.01); *G01N 27/227* (2013.01); *G01N 2027/222* (2013.01)

(58) Field of Classification Search
CPC ............. G01N 33/0037; G01N 27/227; G01N 2027/222; G01N 27/125
See application file for complete search history.

(56) References Cited

U.S. PATENT DOCUMENTS

2010/0139365 A1 *  6/2010  Fix ................. G01N 33/0013
                                                       73/23.31

OTHER PUBLICATIONS

Banerjee, A. et al., "Picowatt Gas Sensing and Resistance Switching in Tunneling Nano-gap Electrodes," 2016 IEEE Sensors, Orlando, FL, USA, 2016, pp. 1-3, doi: 10 1109/ICSENS.2016.7808637.
Kreno, L. E. et al., "Metal-Organic Framework Materials as Chemical Sensors," Chemical Reviews, 2012, vol. 112, pp. 1105-1125.
Li, H-Y. et al., "Functional Metal-Organic Frameworks as Effective Sensors of Gases and Volatile Compounds," Chemical Society Review, 2020, vol. 49, pp. 6364-6401.
(Continued)

*Primary Examiner* — Jennifer Wecker
*Assistant Examiner* — Oyeleye Alexander Alabi
(74) *Attorney, Agent, or Firm* — Kevin W. Bieg

(57) ABSTRACT

Detection and capture of toxic nitrogen oxides ($NO_x$) is important for emissions control of exhaust gases and general public health. The low power sensor provides direct electrically detection of trace (0.5-5 ppm) $NO_2$ at relatively low temperatures (50° C.) via changes in the electrical properties of nitrogen-oxide-capture active materials. For example, the high impedance of MOF-74 enables applications requiring a near-zero power sensor or dosimeter, such as for smart industrial systems and the internet of things, with 0.8 mg MOF-74 active material drawing <15 pW for a macroscale sensor 35 $mm^2$ area.

25 Claims, 17 Drawing Sheets

(56) References Cited

OTHER PUBLICATIONS

Small, L. J. "Reversible MOF-Based Sensors for the Electrical Detection of Iodine Gas," ACS Applied Materials & Interfaces, 2019, vol. 11, pp. 27982-27988.

Small, L. J. and Nenof, T., "Direct Electrical Detection of Iodine Gas by a Novel Metal-Organic-Framework-Based Sensor," ACS Applied Materials Interfaces, 2017, vol. 9, pp. 44649-44655.

Canepa, P. et al., "Structural, Elastic, Thermal, and Electronic Responses of Small-Molecule-Loaded Metal-Organic Framework Materials," Journal of Materials Chemistry A, 2015, vol. 3, pp. 986-995.

Sava Gallis, D. F. et al., "NOx Adsorption and Optical Detection in Rare Earth Metal-Organic Frameworks," ACS Applied Materials Interfaces, 2019, vol. 11, pp. 43270-43277.

Han, X. et al., "Reversible Adsorption of Nitrogen Dioxide within a Robust Porous Metal-Organic Framework," Nature Materials, 2018, vol. 17. pp. 691-696.

Li, J. et al., "Capture of Nitrogen Dioxide and Conversion to Nitric Acid in a Porous Metal-Organic Framework," Nature Chemistry, 2019, vol. 11, pp. 1085-1090.

Schulz, M. et al., "A Calixarene-Based Metal-Organic Framework for Highly Selective $NO_2$ Detection," Angewandte Chemie International Edition, 2018, vol. 57, pp. 12961-12965.

Henkelis, S. E. et al., "A Single Crystal Study of CP0-27 and UTSA-74 for Nitric Oxide Storage and Release," CrystEngComm., 2019, vol. 21, pp. 1857-1861.

Tan, K. et al., "Interaction of Acid Gases $SO_2$ and $NO_2$ with Coordinatively Unsaturated Metal Organic Frameworks M-MOF-74 (M = Zn, Mg, Ni,Co)," Chemistry of Materials, 2017, vol. 29, pp. 4227-4235.

McKinlay, A. C. et al., "Exceptional Behavior over the Whole Adsorption-Storage-Delivery Cycle for NO in Porous Metal Organic Frameworks," Journal of the American Chemical Society, 2008, vol. 130, pp. 10440-10444.

Ebrahim, A. M. et al., "Interactions of $NO_2$ with Zr-Based MOF: Effects of the Size of Organic Linkers on $NO_2$ Adsorption at Ambient Conditions," Langmuir, 2013, vol. 29, pp. 168-174.

McGrath, D. T.et al., "Selective Decontamination of the Reactive Air Pollutant Nitrous Acid via Node-Linker Cooperativity in a Metal-Organic Framework," Chemical Science, 2019, vol. 10, pp. 5576-5581.

De Oliveira, A. et al., "Structural and electronic properties of M-MOF-74 (M = Mg, Co or Mn)," Chemical Physics Letters, 2018, vol. 691, pp. 283-290.

Tan, K. et al., "Competitive Coadsorption of $CO_2$ with $H_2O$, $NH_3$, $SO_2$, NO, $NO_2$, $N_2$, O, and $CH_4$ in M-MOF-74 (M = Mg, Co, Ni): The Role of Hydrogen Ding," Chemical Materials, 2015, vol. 27, pp. 2203-2217.

Becher, J. et al., "Chemical Gradients in Automotive Cu-SSZ-13 Catalysts for NOx Removal Revealed by Operando X-ray Spectrotomography," Nature Catalysis, 2021, vol. 4, pp. 46-53.

Kwak, J. H. et al., "Excellent Activity and Selectivity of Cu-SSZ-13 in the Selective Catalytic Reduction of $NO_x$ with $NH_3$," Journal of Catalysis, 2010, vol. 275, pp. 187-190.

Yu, C. et al., "Manganese-Rich MnSAPO-34 Molecular Sieves as an Efficient Catalyst for the Selective Catalytic Reduction of $NO_x$ with $NH_3$: One-Pot Synthesis, Catalytic Performance, and Characterization," Environmental Science and Pollution Research, 2017, vol. 24, pp. 7499-7510.

Bloch, E. D. et al., "Gradual Release of Strongly Bound Nitric Oxide from $Fe_2(NO)_2(dobdc)$," Journal of the American Chemical Society, 2015, vol. 137, pp. 3466-3469.

Sun, L. et al., "Is Iron Unique in Promoting Electrical Conductivity in MOFs?," Chemical Science, 2017, vol. 8, pp. 4450-4457.

Shekhah, O. et al., "MOF Thin Films: Existing and Future Applications," Chemical Society Reviews, 2011, vol. 40, pp. 1081-1106.

Bradshaw, D. et al., "Metal-Organic Framework Growth at Functional Interfaces: Thin Films and Composites for Diverse Applications," Chemical Society Review, 2012, vol. 41, pp. 2344-2381.

Lee, C. T. and Shin, M. W., "Solvothermal Growth of Mg-MOF-74 Films on Carboxylic Functionalized Silicon Substrate Using Acrylic Acid," Surfaces and Interfaces, 2021, vol. 22, 100845, 6 pages.

U.S. Appl. No. 17/142,443, filed Jan. 6, 2021 and entitled Photoluminescence-Based Detection of Acid Gases Via Rare Earth Metal-Organic Frameworks.

* cited by examiner

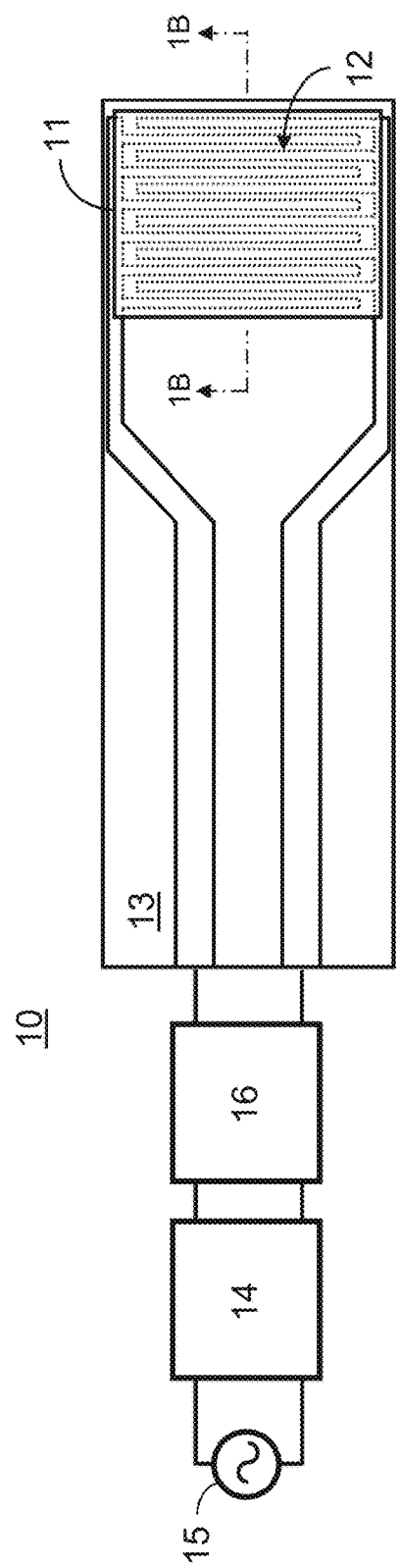
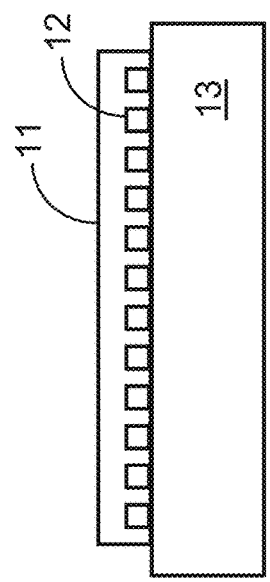
FIG. 1A
FIG. 1B

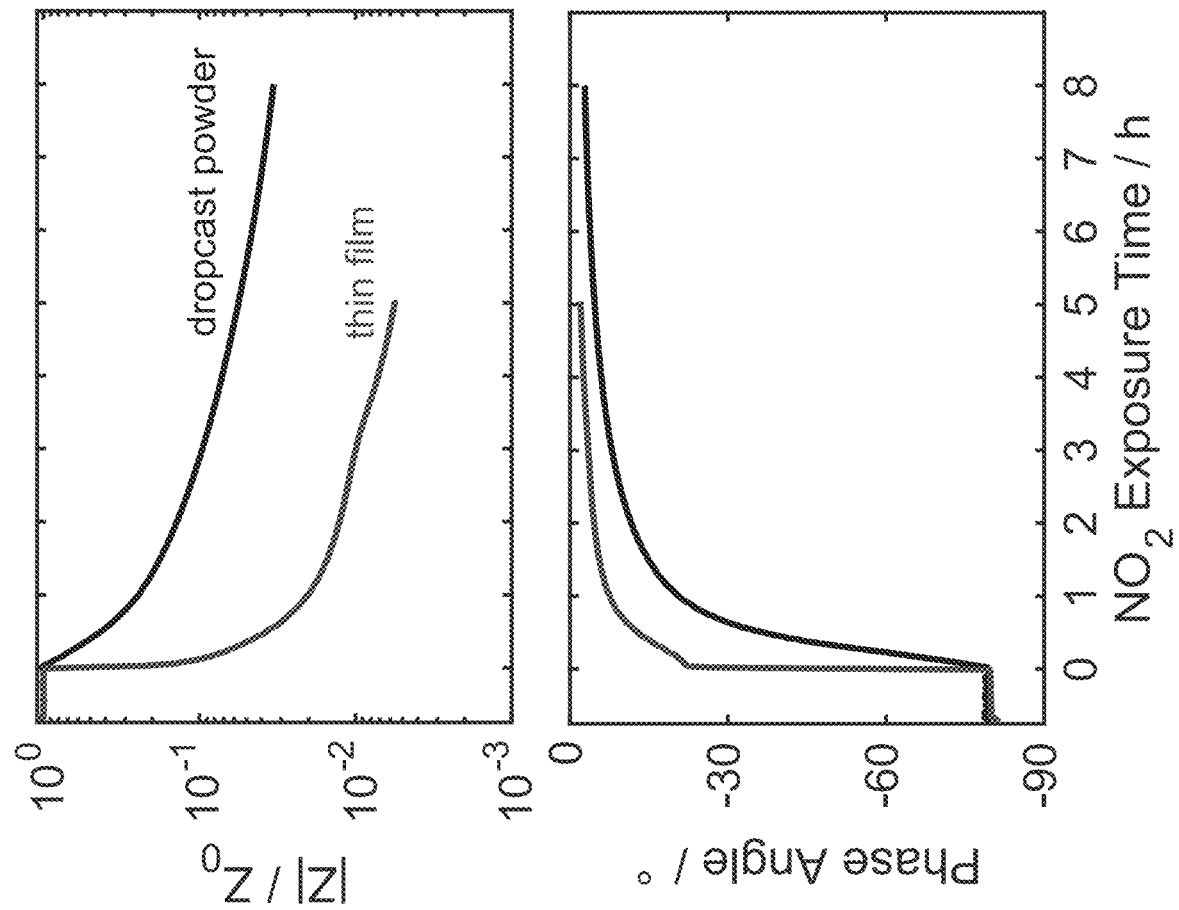

LOW POWER SENSOR FOR NO$_x$ DETECTION

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to toxic gas sensing and, in particular, to a low power sensor for NO$_x$ detection.

BACKGROUND OF THE INVENTION

Nitrogen oxides (NO$_x$) are toxic gases under regulation due to their detrimental environmental effects. See Report on the Environment: Nitrogen Oxides Emissions, US Environmental Protection Agency (2019). Much research has focused on capturing or decomposing them in flue gases or diesel exhaust, with sensing necessary to verify success. See T. Johnson, SAE Int. J. Engines 9, 1258 (2016); and B. Guan et al., Appl. Therm. Eng. 66, 395 (2014). Current NO$_x$ sensing technologies typically use metal oxide sensors at higher temperatures (250-900° C.), or electrochemical cells at near room temperature. See K. P. Ramaiyan and R. Mukundan, J. Electrochem. Soc. 167, 037547 (2020); H. Sasaki et al., in SAE 2010 World Congress & Exhibition, SAE International, Warrendale, Pa., USA (2010); and Drager Sensor & Portable Instruments Handbook, 4$^{th}$ Ed., Drager Safety AG & Co. KGaA, Lubeck, Germany (2018). The power draws of typical sensors mean that they must be hardwired to the power grid or be located in easily serviceable locations for battery replacement. The rise of the "internet of things" (IoT) has increased demand for sensing for environmental monitoring and public health. By decreasing power requirements to "near-zero" (<10 nW), robust, long-lived sensing could be achieved in a wider range of environments. See R. H. Olsson et al., J. Phys.: Conf. Ser. 1407, 012042 (2019). While nanogap-style architectures have been shown successful for near-zero power detection of some organics, the incorporation of nanoporous metal-organic frameworks (MOFs) offer an attractive alternative. See A. Banerjee et al., 2016 IEEE SENSORS, IEEE, Piscataway, N.J. (2016).

MOFs are a class of hybrid organic-inorganic materials composed of metal ions and organic linker molecules. See L. E. Kreno et al., Chem. Rev. 112, 1105 (2012); F. Saraci et al., Chem. Soc. Rev. 49, 7949 (2020); B. F. Hoskins and R. Robson, J. Am. Chem. Soc. 111, 5962 (1989); H.-Y. Li et al., Chem. Soc. Rev. 49, 6364 (2020); and D. Britt et al., Proc. Natl. Acad. Sci. U.S.A 105, 11623 (2008). The nanoporous nature of these materials often imparts extremely high surface areas and makes them ideal for incorporation into membranes. See L. E. Kreno et al., Chem. Rev. 112, 1105 (2012); F. Saraci et al., Chem. Soc. Rev. 49, 7949 (2020); D. Britt et al., Proc. Natl. Acad. Sci. U.S.A 105, 11623 (2008); W.-T. Koo et al., Chem 5, 1938 (2019); M. Fang et al., Membranes 10, 107 (2020); C. Y. Chuah et al., Membranes 10, 74 (2020); C. Y. Chuah et al., Membranes 10, 154 (2020); A. Fuoco et al., Membranes 7, 7 (2017); and L. Upadhyaya et al., Membranes 10, 313 (2020). The high surface area and tunable pore size/shape combined with the ability to alter the composition and impart specific functionalities to tune and optimize their properties make MOFs a very versatile class of materials. See F. Saraci et al., Chem. Soc. Rev. 49, 7949 (2020); H.-Y. Li et al., Chem. Soc. Rev. 49, 6364 (2020); S. E. Henkelis et al., ACS Appl. Mater. Interfaces 12, 22845 (2020); and L. Du et al., J. Am. Chem. Soc. 135, 562 (2013). For these reasons, tailored MOF materials are being extensively investigated for use in chemical separation, catalysts, and sensors. See C. Y. Chuah et al., Membranes 10, 74 (2020); L. E. Kreno et al., Chem. Rev. 112, 1105 (2012); F. Saraci et al., Chem. Soc. Rev. 49, 7949 (2020); C. Y. Chuah et al., Membranes 10, 154 (2020); A. Fuoco et al., Membranes 7, 7 (2017); V. Pascanu et al., J. Am. Chem. Soc. 141, 7223 (2019); P. Garcia-Garcia et al., Chem. Sci. 5, 2979 (2014); A. Herbst and C. Janiak, Cryst Eng Comm. 19, 4092 (2017); I. Liberman et al. J. Am. Chem. Soc. 142, 1933 (2020); H.-Y. Li et al., Chem. Soc. Rev. 49, 6364 (2020); W.-T. Koo et al., Chem 5, 1938 (2019); T.-Y. Luo et al., J. Am. Chem. Soc. 142, 2897 (2020); and L. J. Small and T. M. Nenoff, ACS Appl. Mater. Interfaces 9, 44649 (2017).

Many MOFs are gaining widespread attention as useful materials for selective gas capture and sensing. See L. E. Kreno et al., Chem. Rev. 112, 1105 (2012); H.-Y. Li et al., Chem. Soc. Rev. 49, 6364 (2020); and L. J. Small et al., ACS Appl. Mater. Interfaces 11, 27982 (2019). MOFs have previously been used for direct electrical sensing of gases. Changes in electrical properties of ZIF-8 and MFM-300(X) (X=Al, Fe, In, Sc) have been previously used to electrically detect the presence of I$_2$ gas in air, demonstrating up to a $10^6 \times$ decrease in MOF resistance upon I$_2$ adsorption. See L. J. Small and T. M. Nenoff, ACS Appl. Mater. Interfaces 9, 44649 (2017); and L. J. Small et al., ACS Appl. Mater. Interfaces 11, 27982 (2019). Other groups have used MOFs to create direct electrical sensors for SO$_2$ using MFM-300 (In), NO with Cu$_3$HHTP$_2$ and NiHTTP$_2$, CO$_2$ with a Co-MOF-74 composite or Cu$_3$(hexaiminobenzene)$_2$, alcohols with HKUST-1, and hydrocarbons with Cu[Ni[2,3-pyrzin-edithiolate)$_2$], or Cu-TCPP/Cu-HHTP. See V. Chernikova et al., J. Mater. Chem. A 6, 5550 (2018); M. K. Smith et al., Chem. Mater. 28, 5264 (2016); 1. Strauss et al., ACS Appl. Mater. Interfaces 11, 14175 (2019); 1. Stassen et al., ACS Cent. Sci. 5, 1425 (2019); S. Achmann et al., Sensors 9, 1574 (2009); M. L. Aubrey et al., J. Amer. Chem. Soc. 141, 5005 (2019); and M.-S. Yao et al., Angew. Chem. Int. Ed. 58, 14915 (2019). Previously, several MOF materials have been shown to selectively capture NO$_2$, including RE-DOBDC (where RE is a rare earth element and DOBDC is dihydroxyterephthalic acid), MFM-300(AI), MFM-520, [Zr$_6$O$_4$(OH)$_4$(FA)$_6$]$_2$(calixarene)$_3$, MOF-74, UiO-66, and UiO-67. See D. F. Sava Gallis et al., ACS Appl. Mater. Interfaces 11, 43270 (2019); Han et al., Nat. Mater. 17, 691 (2018); J. Li et al., Nat. Mater. 11, 1085 (2019); M. Schulz et al., Angew. Chem., Int. Ed. 57, 12961 (2018); S. E. Henkelis et al., Cryst. Eng. Commun. 21, 1857 (2019); K. Tan et al., Chem. Mater. 29, 4227 (2017); A. C. McKinlay et al., J. Am. Chem. Soc. 130, 10440 (2008); A. M. Ebrahim et al., Langmuir 29, 168 (2013); and D. T. McGrath et al., Chem. Sci. 10, 5576 (2019).

However, most of these MOF materials have not yet been demonstrated as effective sensing materials through direct electrical measurements.

SUMMARY OF THE INVENTION

The present invention a nitrogen oxide sensor, comprising an electrically insulating substrate; a pair of interdigitated electrodes (IDEs) disposed on the substrate; a nitrogen-oxide-capture film disposed on the array of interdigitated electrodes and the substrate; and a frequency response analyzer for measuring the impedance response of the nitrogen-oxide-capture film when nitrogen oxide is absorbed in the nitrogen-oxide-capture film and an alternating voltage is applied to the array of interdigitated electrodes. For example, the nitrogen-oxide-capture film can comprise a metal-organic framework (MOF) or microporous aluminosilicate (zeolite) material.

Key attributes for long-lived, near-zero power chemical sensors include: (1) extremely high resistance ($>10^9\Omega$) in the activated state, (2) strong active material-analyte binding to prevent escape of captured analytes, and (3) large per-unit-cell adsorption capacity coupled with (4) a favorable redox potential of the analyte with respect to the active capture material. These characteristics enable a low power (e.g., <15 pW) sensor or dosimeter with irreversible analyte capture and a corresponding large change in MOF electrical response. While many MOFs satisfy criterion (1), evaluation and optimization of the remaining characteristics under complex gas streams is needed for robust real-life sensors.

As a first example of the invention, sensors were fabricated by dropcasting M-MOF-74 (M=Co, Mg, Ni) as the active nitrogen-oxide-capture material onto an IDE/glass substrate. Differences in electrical response to $NO_2$ between the M-MOF-74 analogues were attributed to both the adsorption capacity and chemical interactions between the $NO_2$ and MOF. The magnitude of the electrical response observed is ordered Ni >Co >Mg, with Ni-MOF-74 providing 725× decrease in resistance at 5 ppm $NO_2$ and a $NO_2$ detection limit <0.5 ppm, levels relevant for industrial and public health. Furthermore, the Ni-MOF-74-based sensor had a superior electrical response in its selectivity to $NO_2$ over common competing gases such as $N_2$, $SO_2$, and ambient air (25° C., 50% RH, 400 pm $CO_2$) heated to 50° C.

As a second example of the invention, sensors were fabricated by growing thin films of M-MOF-74 on functionalized substrates. A two-step surface functionalization procedure on a Pt-IDE on glass substrate resulted in a terminal carboxylate group, with both steps confirmed through infrared spectroscopic analysis. This surface functionalization allowed the MOF materials to grow largely in a uniform manner over the substrate surface and coalescing as a thin film over the Pt sensing electrodes. Each MOF grew as a continuous but non-defect free thin film with overlapping polycrystallites across the exposed glass and the IDE surfaces. A Ni-MOF-74 thin film sensor was exposed to 5 ppm $NO_2$ and the impedance magnitude was observed to decrease 123× in 4 h, with a larger change in impedance and a faster and more sensitive response compared to the bulk material of the dropcast powder sensor.

BRIEF DESCRIPTION OF THE DRAWINGS

The detailed description will refer to the following drawings, wherein like elements are referred to by like numbers.

FIG. 1A is a top-view schematic illustration of a low power sensor for the direct electrical detection of $NO_x$. FIG. 1B is a cross-sectional side-view schematic illustration of the $NO_x$ sensing region of the sensor.

FIG. 8A shows Ni-MOF-74 $R_{MOF}$ versus time for exposure to 5, 2, 1, or 0.5 ppm $NO_2$. The $NO_2$ exposure time is highlighted in gray. FIG. 8B shows the change in $R_{MOF}$ for M-MOF-74 (M=Co, Mg, Ni) after a 0.75 h $NO_2$ exposure. FIG. 8C shows the reversibility (% change) in $R_{MOF}$ for M-MOF-74 (M=Co, Mg, Ni) 0.75 h after removal of $NO_2$. No statistically significant change was observed for Mg-MOF-74 at 0.5 ppm in FIG. 8B, causing it to be omitted from FIG. 8C.

FIG. 9A shows 8 h exposures. FIG. 9B shows a comparison of response of extended air-exposure combined with subsequent $NO_x$ exposure. Here, "air" is ambient atmosphere (25° C.) of 50% relative humidity, 400 ppm $CO_2$, and 21% oxygen, and then heated to 50° C.

FIG. 11A shows the full IR spectra. FIG. 11B shows the spectra zoomed in to 1400-2000 $cm^{-1}$ to highlight peaks formed after functionalization with aminosilanes (N—H peak at 1560 $cm^{-1}$) and succinic anhydride (C=O peak at 1690 $cm^{-1}$).

FIGS. 17A and 17B show a comparison of the electrical impedance (100 mHz) over time of an IDE with a Ni-MOF-74 MOF thin film grown on it versus an IDE with bulk Ni-MOF-74 powder dropcast onto it. Both IDEs were exposed to 5 ppm $NO_2$ in $N_2$ at 50° C.

DETAILED DESCRIPTION OF THE INVENTION

Figures 2A, 2B, 2C, 2D:
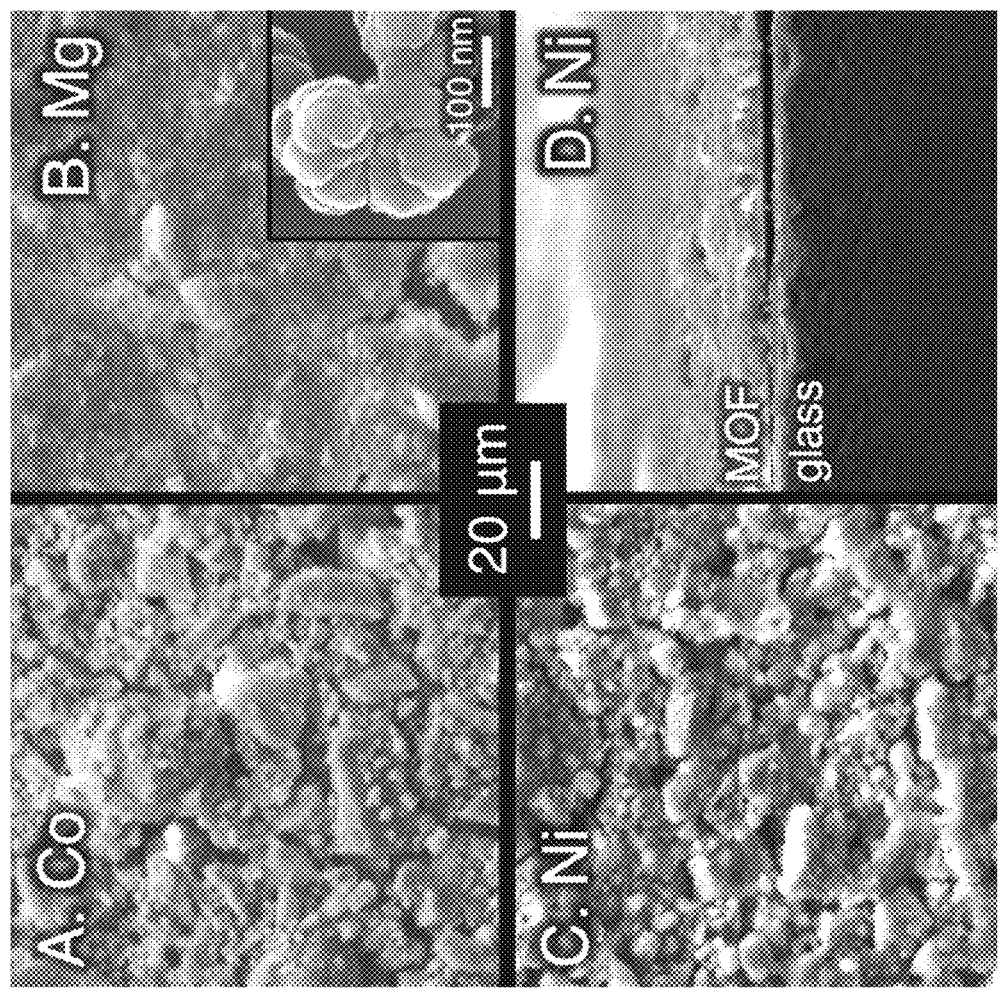
FIG. 2A is a plan-view SEM micrograph of Co-MOF-74 powder dropcast onto an IDE.
FIG. 2B is a plan-view SEM micrograph of Mg-MOF-74.
FIG. 2C is a plan-view SEM micrograph of Ni-MOF-74.
FIG. 2D is a cross-sectional micrograph of the Ni-MOF-74 film shown in FIG. 2C.

As shown in FIGS. 1A and 1B, the low power $NO_x$ sensor 10 comprises a nitrogen-oxide-capture film 11 disposed on interdigitated electrodes (IDEs) 12. The nitrogen-oxide-capture material is preferably a metal-organic framework (MOF) or a microporous aluminosilicate (zeolite). The IDEs 12 comprise a pair interlocking comb-shaped arrays of metallic electrodes deposited on the surface of an electrically insulating substrate 13. The substrate is preferably more electrically insulating (i.e., has a higher resistivity) than the nitrogen-oxide-capture material. For example, the substrate can be a high resistance silica glass. Impedance spectroscopy can be used to measure the electrical impedance of the coated IDEs over a range of frequencies. Therefore, the sensor 10 can further comprise a frequency response analyzer 14 for measuring the impedance response of the MOF film when an AC voltage 15 is applied to the IDEs 12. The impedance can be related to the capacitance and conductivity of the $NO_x$-capture material. When an alternating voltage is applied to the IDE, some energy is stored by the capacitance, and some is dissipated by the resistance effects. Therefore, the resulting current will exhibit a phase lag. The capacitance effect is known as the permittivity (or dielectric constant), and the resistive effect as dielectric loss. The sensor can be operated at an AC frequency corresponding to a RC transition frequency that leverages the capacitive component of the $NO_x$-capture material to increase the signal strength while still enabling the larger signal change associated with the DC resistance to be calculated. In materials where the dielectric loss is very small and the permittivity is large, a high impedance interface 16 can be connected in series with the frequency response analyzer 14 to provide a more accurate impedance measurement. The high impedance interface 16 enables a reference measurement to be obtained on precision internal reference capacitors which are automatically substituted for the sample; a second measurement is made, this time on the sample itself. The two results are used to derive an accurate measurement of the permittivity of the $NO_x$-capture material—in effect, the first measurement is used to eliminate the effects of extraneous capacitance.

A well-known family of MOFs, MOF-74 (CPO-27) has been extensively studied for the interaction of the metal center (Mg, Ni, Co, Zn) with different acid gases, such as $NO_x$, $SO_x$, $CO_2$, and $H_2O$, and the competitive binding of each investigated by both computational and experimental methods. See K. Tan et al., *Chem. Mater.* 29, 4227 (2017). M-MOF-74 are a series of isostructures with a variety of metals (M) and the same organic ligand, 2,5-dihydroxyterephthalic acid (DHTP). Current literature has highlighted the uniqueness of electronic structure in M-MOF-74 as a function of metal choice and response to various adsorbed gases. See A. de Oliveira et al., *Chem. Phys. Lett.* 691, 283 (2018); K. Tan et al., *Chem. Mater.* 27, 2203 (2015); and K. Tan et al., *Chem. Mater.* 29, 4227 (2017). Each adsorbed gas has been calculated to modify M-MOF-74 electronic structures to a varying degree, indicating the possibility for sensing of unique chemical species. For application in electrical sensing, the change in electronic structure, due to gas adsorption, modifies the effective masses of electrons and holes, therefore changing the conductivity of the MOF material. This is highlighted in Zn-MOF-74 when comparing how weak ($H_2$, $CH_4$) and strong ($H_2O$, $CO_2$) interactions are calculated to result in modified effective masses. See P. Canepa et al., *J. Mater. Chem. A* 3, 986 (2015). When discussing gases such as $NO_x$, they are found to strongly interact with M-MOF-74 materials, leading to an expectation that the conductivity in M-MOF-74 will be modified following gas exposure. This is confirmed as adsorption of $NO_2$ in M-MOF-74 (M=Mg, Zn) shows $NO_2$ takes electronic charge from the MOF and valence electron density is delocalized across the adsorbed gas and interacting organic linkers. See P. Canepa et al., *J. Mater. Chem. A* 3, 986 (2015).

Another MOF that can be used with the invention includes RE-DOBDCs (where RE is a rare earth element and DOBDC is dihydroxyterephthalic acid). These RE-DOBDC MOFs have recently been shown to have strong durability to the adsorption of $NO_x$ and have been used for the photoluminescence-based detection of acid gases. See U.S. application Ser. No. 17/142,443, filed Jan. 6, 2021, which is incorporated herein by reference.

A number of microporous aluminosilicates are also suitable as $NO_x$-capture materials of the present invention. For example, a number of aluminosilicate SSZ-13 (e.g., Cu-SSZ-13, Ni-SSZ-13) and silicoaluminaphosphate (e.g., MnSAPO-34) zeolites have been demonstrated to be capable of eliminating $NO_x$ via selective catalytic reduction (SCR) by ammonia. See J. Becher et al., *Nat. Catal.* 4, 46 (2021); J. H. Kwak et al., *J. Catal.* 275, 187 (2010); C. Yu et al., *Environ. Sci. Pollut. Res. Int.* 24(8), 7499 (2017); and WO 2011/064666 to G. R. Chandler et al., which are incorporated herein by reference.

Direct electrical detection of gaseous analytes by MOFs can be performed through either a change in the capacitance or resistance of the MOF-containing sensor. Changes in capacitance are typically measured by an alternating voltage at relatively high frequency (e.g. 1 MHz), such as the $SO_2$ sensor Chernikova et al. built to successfully detect ppb levels of $SO_2$. See V. Chernikova et al., *J. Mater. Chem. A* 6, 5550 (2018). Changes in capacitance for MOF-based sensors are typically small, however, as the change is based on the real permittivity of the MOF having adsorbed one gas (e.g. $N_2$) versus another (e.g. $SO_2$). On the other hand, changes in MOF resistance in response to a gaseous analyte are typically recorded as DC measurements, e.g. a chemiresistor. See I. Stassen et al., *ACS Cent. Sci.* 5, 1425 (2019); M. L. Aubrey et al., *J. Amer. Chem. Soc.* 141, 5005 (2019); and M.-S. Yao et al., *Angew. Chem. Int. Ed.* 58, 14915 (2019). While this approach offers potentially large changes in signal for the right MOF-analyte combinations, it can be technically challenging, as many MOFs possess resistivities approaching those of common insulators, such as alumina. See L. J. Small and T. M. Nenoff, *ACS Appl. Mater. Interfaces* 9, 44649 (2017); L. J. Small et al., *ACS Appl. Mater. Interfaces* 11, 27982 (2019); A. A. Talin et al., *Science* 343, 66 (2014); and L. Sun et al., *J. Amer. Chem. Soc.* 137, 6164 (2015). Therefore, many groups have worked towards identifying lower resistivity MOFs. See I. Stassen et al., *Chem. Soc. Rev.* 46, 3185 (2017); and S. K. Bhardwaj et al., *J. Mater. Chem. A* 6, 14992 (2018). A downside to decreasing the MOF resistivity, however, is an increase in the sensor's power consumption. While resistive components dissipate power, purely capacitive (e.g. reactive, or imaginary impedance) components do not. See E. Barsoukov and J. R. Macdonald, *Impedance Spectroscopy: Theory, Experiment, and Applications*, 2nd Ed., Wiley, Hoboken, N.J., USA (2005).

The present invention marries the high signal strength and low power consumption of a capacitive $NO_x$-capture sensor with the large signal change of a resistive $NO_x$-capture sensor. The invention uses a hybrid approach whereby impedance spectroscopy is first applied in the lab to understand the AC frequency response across a wide range (1 mHz-1 MHz), and then used to extrapolate the DC resistance of the $NO_x$-capture sensor. From this data, a single RC transition frequency (e.g. 100 mHz) is selected, leveraging the capacitive component of the $NO_x$-capture material to increase the signal strength while still receiving information about the $NO_x$-capture material's DC resistance.

With this hybrid approach, both the high resistivity and $NO_x$ selectivity of an exemplary M-MOF-74 (M=Co, Mg, Ni) was leveraged to create an active material for a near-zero power sensor which detects the presence of $NO_x$ through changes in the electrical properties of MOF-74. MOF-74 is a well-known $NO_x$ adsorbent, with different metal centers imparting differing $NO_x$-adsorbing abilities. See K. Tan et al., *Chem. Mater.* 29, 4227 (2017); K. Tan et al., *Chem. Mater.* 27, 2203 (2015); and E. D. Bloch et al., *J. Amer. Chem. Soc.* 137, 3466 (2015). Moreover, the electronic structure of activated MOF-74 has been well-studied, offering insights for changes in electrical resistivity upon $NO_x$ adsorption. See L. Sun et al., *Chem. Sci.* 8, 4450 (2017).

As will be described below, both dropcast powder and functionalized IDE sensors were fabricated that leverage the high signal strength and low power consumption of a capacitive MOF-74 based sensor with the large signal change of a resistive MOF sensor. A unique acid gas test chamber was designed and built for flexibility in sensor testing. The electrical changes of M-MOF-74 (M=Co, Mg, Ni) sensors were quantified in response to trace $NO_2$ (0.5-5 ppm) and significant differences were demonstrated in electrical response depending on the metal center used. These differences are shown to be related to the structure of the MOF and the adsorption mechanisms with $NO_2$.

Example: Dropcast Powder MOF-Based Sensor

As an example of the invention, a series of sensors were fabricated by dropcasting MOF-74 powders on IDEs on glass substrates. In order to evaluate the influence of the MOF-74 metal center on $NO_2$ sensing ability, a series of IDEs were coated with M-MOF-74 (M=Co, Mg, Ni), activated at 200° C. under vacuum, and interrogated with impedance spectroscopy at varying $NO_2$ concentrations. MOF activation, $NO_2$ exposure, and electrical testing all occurred in the same test chamber; once activated the MOF was maintained in an inert environment due to its hydrophilic nature and therefore never exposed to ambient lab atmosphere or humidity.

Sensor Fabrication

M-MOF-74 was synthesized using a literature procedure, with minor alterations. See S. M. Vornholt et al., *Dalton Trans.* 46, 8298 (2017); S. E. Henkelis et al., *Cryst. Eng. Commun.* 21, 1857 (2019); and L. J. Small et al., Adv. *Funct. Mater.* 2006598, 1 (2020).

To synthesize Co-MOF-74, cobalt acetate tetrahydrate (1.28 g, 5.00 mmol) was dissolved in methanol (18 mL) with stirring. 2,5-dihydroxyterephthalic acid (0.5 g, 2.50 mmol) was dissolved in sodium hydroxide (1 M, 10 mL) and added dropwise to the salt solution in 1 mL aliquots over 5 mins. The reaction solution was heated to reflux for 16 hr and then allowed to cool. The powder was collected by filtration, washed with methanol (2×100 mL) and water (2×100 mL) and allowed to dry overnight in air.

To synthesize Mg-MOF-74, magnesium nitrate hexahydrate (1.25 g, 5.00 mmol) was dissolved in methanol (18 mL) with stirring. 2,5-dihydroxyterephthalic acid (0.5 g, 2.50 mmol) was dissolved in sodium hydroxide (1 M, 10 mL) and added dropwise to the salt solution in 1 mL aliquots over 5 mins. The reaction solution was heated to reflux for 16 hr and then allowed to cool. The powder was collected by filtration, washed with methanol (2×100 mL) and water (2×100 mL) and allowed to dry overnight in air.

To synthesize Ni-MOF-74, nickel acetate tetrahydrate (1.24 g, 5.00 mmol) was dissolved in water (14 mL) with stirring. 2,5-dihydroxyterephthalic acid (0.5 g, 2.50 mmol) was dissolved in sodium hydroxide (1 M, 10 mL) and added dropwise to the salt solution in 1 mL aliquots over 5 mins. The reaction solution was heated to reflux for 16 hr and then allowed to cool. The powder was collected by filtration, washed with methanol (2×100 mL) and water (2×100 mL) and allowed to dry overnight in air.

For use in the dropcast powder sensor, Co-MOF-74 and Ni-MOF-74 were ground into a fine powder using a mortar and pestle. Mg-MOF-74 was used as-synthesized.

Platinum IDEs on glass substrates were obtained from DropSens (product G-IDEPT10). These IDEs contain 125 pairs of platinum lines 250 nm thick and 10 µm wide with a spacing of 10 µm between lines. The IDEs were cleaned under $N_2$ flow, and their impedance magnitude at 100 mHz was verified to be greater than $3 \times 10^{10} \Omega$. In a 10 mL glass vial, 25 mg of MOF-74 powder and 1 mL acetone were mixed. The mixture was sealed and stirred vigorously for 30 minutes, after which 12.5 µL was pipetted onto the active area of the IDE. The IDE was allowed to dry at room temperature for 5 mins, followed by deposition of another 12.5 µL of the MOF suspension. This resulted in 0.8 mg of MOF-74 being deposited on the active area of the IDE (~35 $mm^2$).

MOF-74-coated IDEs were loaded into a custom-built $NO_x$ exposure chamber that enabled MOF activation and subsequent in situ electrical testing under varying $NO_2$ concentrations without exposure to lab atmosphere. Variable $NO_2$ concentrations were achieved by diluting a 5 ppm $NO_2$ gas stream with a pure UHP $N_2$ at 500 sccm total gas flow.

To ensure that the bulk MOF-74 materials were crystalline, phase pure and bench stable, each MOF was investigated initially by powder X-ray diffraction (XRD). Each powder pattern highlighted the two primary diffraction peaks for MOF-74 at 6.8 and 12° 2θ, corresponding to the 14 Å MOF pore. Upon dropcasting the MOF suspended in acetone onto the IDE/glass, all diffraction peaks' intensities were vastly reduced due to the mass loading (0.8 mg), with the amorphous nature of the glass (15-40° 2θ) dominating the XRD pattern. However, the two primary peaks were still able to be identified. Additionally, a sharp peak near 40° 2θ corresponded to the platinum electrodes of the IDE.

upon exposure to 5 ppm $NO_2$ for 8 h, with Co-MOF-74 and Mg-MOF-74 showing changes in $R_{MOF}$ of only 63.8× and 20.2×, respectively. All sensors displayed similar impedance responses before $NO_2$ exposure (23.5-25.3 GΩ at 100 mHz, n=22), regardless of M-MOF-74 analog, and blank IDEs had no response to $NO_2$.

TABLE 1

Comparison of sensor impedance at 100 mHz for M-MOF-74 (M = Co, Mg, Ni) after activation ($Z_{activated}$) to that after exposing to 5 ppm $NO_2$ at 50° C. for 8 h ($Z_{NO2}$). From the sensor impedances, the corresponding DC resistances of the M-MOF-74 films ($R_{MOF}$) are derived as-activated ($R_{activated}$) and after $NO_2$ exposure ($R_{NO2}$). The corresponding power consumptions are calculated similarly, for M-MOF-74 as-activated and after $NO_2$ exposure. Uncertainties are one standard deviation.

| M-MOF-74 | $\|Z_{activated}\|$/ GΩ | $\|Z_{NO2}\|$/ GΩ | $\|Z_{activated}\|$/ $\|Z_{NO2}\|$ | $R_{activated}$/ GΩ | $R_{NO2}$/ GΩ | $R_{activated}$/ $R_{NO2}$ | Power As-activated/ pW | Power $NO_2$-loaded/ pW |
|---|---|---|---|---|---|---|---|---|
| Co | 23.3 ± 0.3 | 7.06 ± 1.60 | 3.40 ± 0.69 | 548 ± 101 | 8.75 ± 2.59 | 63.8 ± 6.3 | 2.05 ± 0.01 | 1.59 ± 0.25 |
| Mg | 24.8 ± 0.2 | 12.1 ± 0.9 | 2.93 ± 0.2 | 553 ± 117 | 177 ± 68 | 20.2 ± 1.6 | 2.25 ± 0.12 | 1.67 ± 0.44 |
| Ni | 25.0 ± 0.5 | 0.747 ± 0.076 | 33.7 ± 3.0 | 545 ± 15 | 0.758 ± 0.082 | 725 ± 79 | 2.17 ± 0.06 | 13.5 ± 1.3 |

The M-MOF-74 powders dropcast on IDEs were evaluated in scanning electron microscope (SEM). Characteristic micrographs are shown in FIGS. 2A-2D. Co- and Ni-MOF-74 contained a wide range of crystallite sizes, from 100's of μm to 100 nm. Mg-MOF-74, on the other hand, displayed individual crystallites on the order of 100 nm. Film thickness of the dropcast powder coatings was determined to be on the order of 10 μm.

Impedance Response

Figures 3A, 3B:
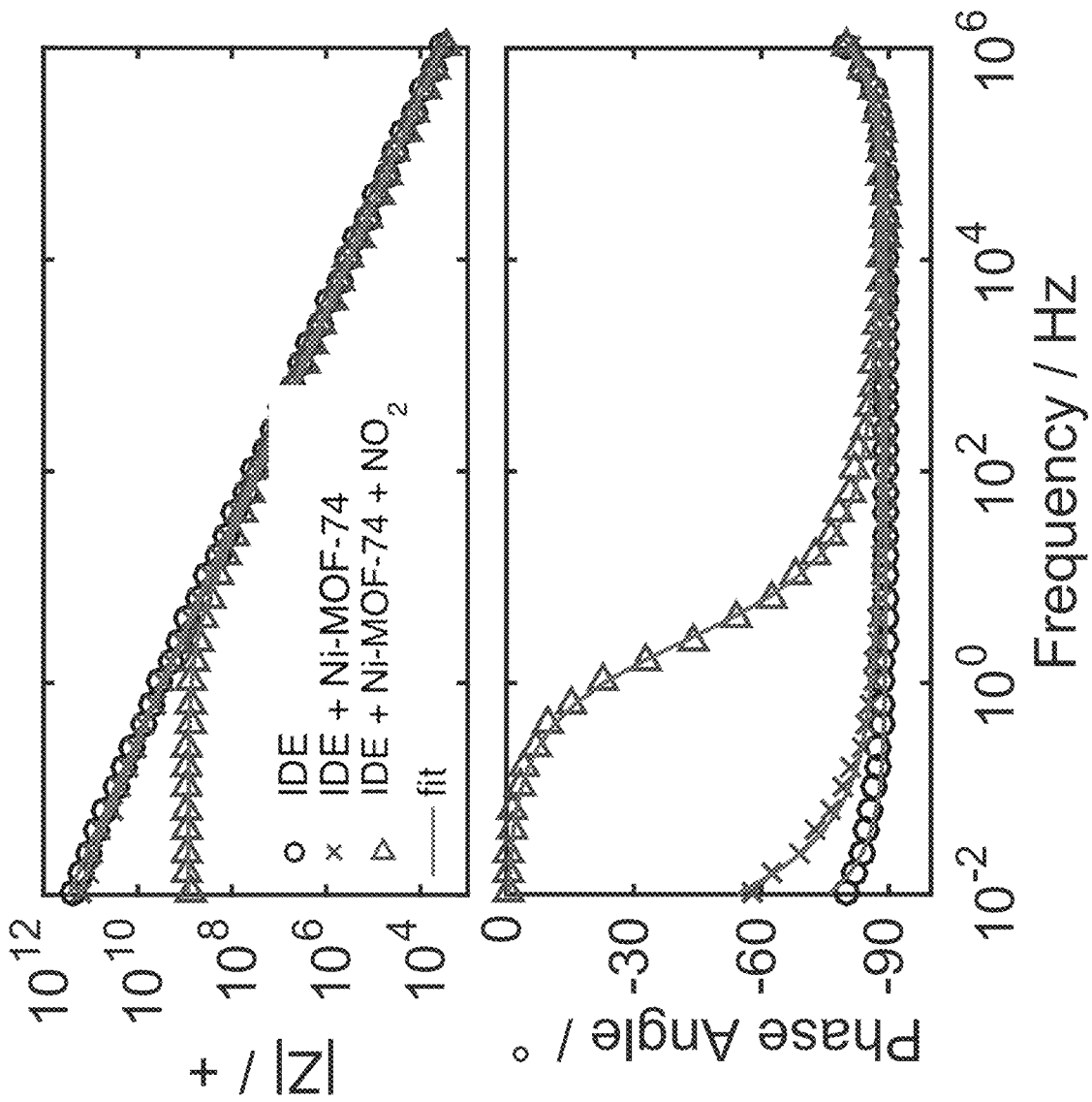
FIGS. 3A and 3B are graphs of impedance spectra (magnitude and phase angle, respectively) of the same IDE (1) blank, (2) coated with Ni-MOF-74 and activated, and (3) coated with Ni-MOF-74, activated, and exposed to 5 ppm $NO_2$ for 8 h. Solid lines represent fits to equivalent circuits.
Figures 4C, 4D:
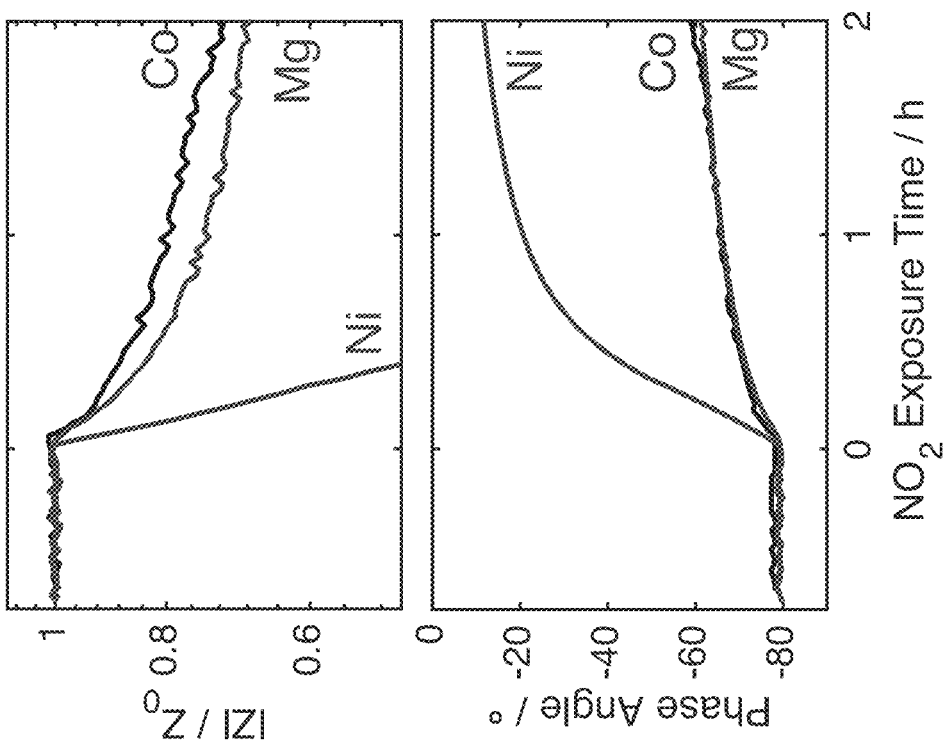
FIGS. 4C and 4D are impedance spectra zoomed in to t=0 h, revealing the rapid sensor response. Zo=23.1, 25.2, and 25.0 GW for Co-MOF-74, Mg-MOF-74, and Ni-MOF-74, respectively.
Figures 4A, 4B:
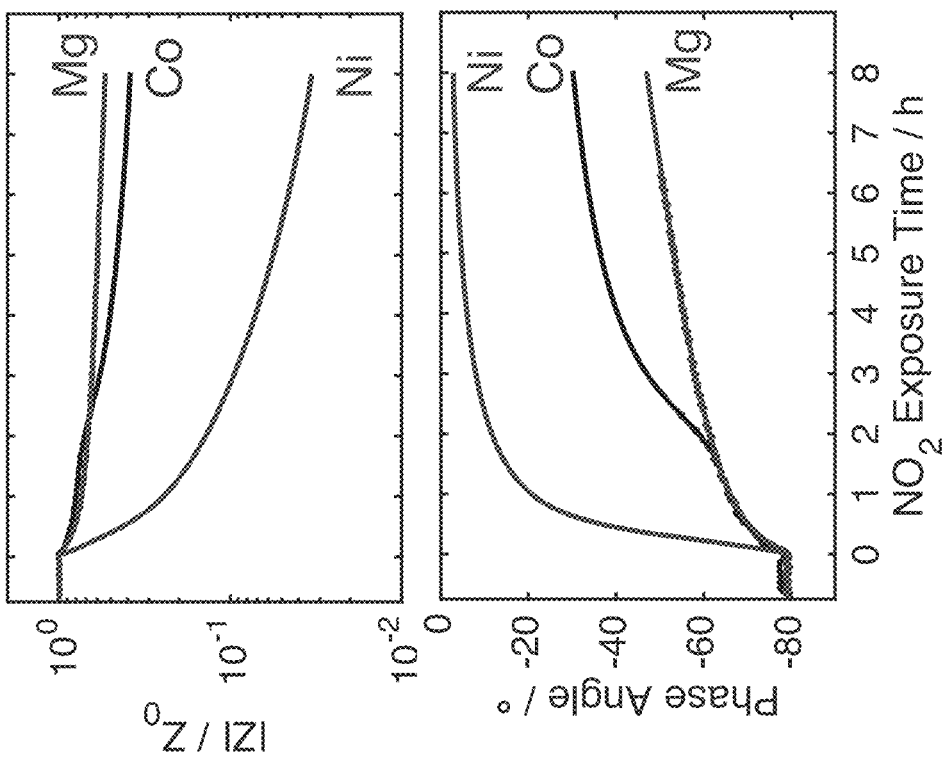
FIGS. 4A and 4B are graphs of impedance (magnitude and phase angle, respectively) at 100 mHz for IDEs coated with M-MOF-74 (M=Co, Mg, Ni) during exposure to 5 ppm $NO_2$ at 50° C.

Impedance spectra were recorded using a Solartron 1260 Frequency Response Analyzer connected in series with Solartron 1296 Dielectric Interface, utilizing the internal reference capacitors for every measurement. Typical impedance spectra for the dropcast powder sensors are shown in FIGS. 3A and 3B. With only a blank IDE, the response is both very high impedance ($|Z|>10^{11}$Ω at 10 mHz) and highly capacitive (θ~−90°). Addition of activated Ni-MOF-74 slightly decreases |Z| and increases θ at low frequencies, indicating that the DC resistance of the Ni-MOF-74 film is less than that of the glass substrate. Upon exposing Ni-MOF-74 to 5 ppm $NO_2$ a change in impedance response is readily detected within 3 minutes, as shown in FIGS. 4A-4D, on par with the gas exchange rate of the experimental setup. By 8 h, the impedance response had drastically changed; the IDE exhibited a 33.7× decrease in |Z| at 100 mHz and a transition in low frequency response from capacitive (θ~−90°) to resistive (θ~0°), as seen in FIGS. 4A and 4B. This change signaled a decrease in MOF film resistance upon adsorption of $NO_2$. Additionally, the Ni-MOF-74 visually appeared darker after $NO_2$ exposure. Similar color changes and impedance responses were observed for Co-MOF-74 and Mg-MOF-74, though the order of magnitude differed. The exact changes in Z at 100 mHz for M-MOF-74 before and after exposure to $NO_2$ are compiled in Table 1, labeled $Z_{activated}$ and $Z_{NO2}$, respectively. Upon reactivation, the impedance response returned to the previously activated value. A parallel RC circuit, shown in FIG. 5, was fit to account for the capacitance and resistance of the substrate, while extracting the DC (f=0) capacitance and resistance ($R_{MOF}$) of the MOF film. The results of these fits are overlaid in FIGS. 3A and 3B, and the resulting MOF film resistances ($R_{MOF}$) are compiled in Table 1 and FIG. 6. Ni-MOF-74 displays the largest decrease (725×) in $R_{MOF}$ Power Consumption These $NO_2$ sensors exhibit incredibly low power consumption for the active component of a chemical sensor. Despite their macro-scale (35 mm², 0.8 mg MOF-74), all M-MOF-74 sensors dissipated less than 2.25 pW at 100 mHz as-activated, and less than 13.5 pW after 8 h of $NO_2$ exposure. Here power consumption, P, at 100 mHz was calculated as $P=V^2(|Z| \cos \theta)^{-1}$, where V is the AC voltage, Z is the impedance magnitude, and θ is the phase angle. See E. Barsoukov and J. R. Macdonald, *Impedance Spectroscopy: Theory, Experiment, and Applications,* 2nd Ed., Wiley, Hoboken, N.J., USA (2005). Importantly, and with far reaching industrial applications, the picowatt power expense of these MOF-based active materials far exceed DARPA's 10 nW threshold for near-zero power applications. See R. H. Olsson et al., *J. Phys.: Conf. Ser.* 1407, 012042 (2019).

$NO_2$ Adsorption Capacity

The different electrical responses to $NO_2$ are directly related to both the $NO_2$ adsorption capacity and how the $NO_2$ chemically interacts with each M-MOF-74. The $NO_2$ adsorption capacity of M-MOF-74 is ordered Mg<Co~Ni. See D. Cattaneo et al., *Dalton Trans.* 45, 618 (2016); and D. Cattaneo et al., *RSC Adv.* 6, 14059 (2016). Considering electronic structure calculations of MOF-74 from several different studies, it is apparent that the metal centers in both Ni- and Co-MOF-74 contribute significantly to electronic states at the band gap edges, while $Mg^{2+}$ in Mg-MOF-74 does not. See L. Sun et al., *J. Amer. Chem. Soc.* 137, 6164 (2015); L. Sun et al., *Chem. Sci.* 8, 4450 (2017); and A. de Oliveria et al., *Chem. Phys. Lett.* 691, 283 (2018). Because $NO_2$ has been shown to adsorb to the metal sites, changes to the resistivity of Mg-MOF-74 upon $NO_2$ adsorption are expected to be significantly smaller. See L. Sun et al., *J. Amer. Chem. Soc.* 137, 6164 (2015); and L. Sun et al., *Chem. Sci.* 8, 4450 (2017). Thus, the fewer $NO_2$ molecules that adsorb to Mg-MOF-74 are expected to contribute less to changes in $R_{MOF}$ than in Co- and Ni-MOF-74, consistent with the data shown in Table 1 and FIG. 6.

Upon adsorption, $NO_2$ and M-MOF-74 interact in several ways, similar to $NO_2$ interaction with a metal oxide. See K. Tan et al., *Chem. Mater.* 29, 4227 (2017); K. Tan et al., *Chem. Mater.* 27, 2203 (2015); M. Mihaylov and K. Hadjiivanov, *Chem. Commun.* 2200 (2004); and B. Djonev et al., *J. Chem. Soc. Faraday Trans.* 93, 4055 (1997). First, $NO_2$ molecularly adsorbs to the MOF's coordinatively unsaturated metal sites, with partial charge transfer from the metal site to the adsorbed $NO_2$. See K. Tan et al., *Chem. Mater.* 29, 4227 (2017). The adsorbed $NO_2$ can then dissociate into adsorbed $NO_3^-$ and NO gas. It can be assumed that NO gas binds more strongly to $Ni^{2+}$ and $Co^{2+}$ via π-back-donation, and less strongly to $Mg^{2+}$, which lacks d-electrons. See K. Tan et al., *Chem. Mater.* 29, 4227 (2017); and D. Cattaneo et al., *RSC Adv.* 6, 14059 (2016). Thus, a complex equilibrium of $NO_2$, NO, and $NO_3$ exists adsorbed to the MOF metal sites.

The data suggests that the relative $NO_2/NO/NO_3^-$ equilibrium is specific to each M-MOF-74, and the interaction of that mixture with the MOF electronic structure is responsible for the different observed changes in $R_{MOF}$. While binding of pure NO has been shown to be similar for Co- and Ni-MOF-74, the interaction between $NO_2$ is different, more heavily influenced by the differences in MOF electronic structure. See A. C. McKinlay et al., *J. Amer. Chem. Soc.* 130, 10440 (2008); and K. Tan et al., *Chem. Mater.* 27, 2203 (2015). Tan et. al observed in their IR data, a significantly larger relative intensity of $NO_3^-$ as compared to $NO_2$ for Ni-MOF-74, than Co-MOF-74 after $NO_2$ adsorption. See K. Tan et al., *Chem. Mater.* 29, 4227 (2017). The generation of more ionic species for Ni-MOF-74 are likely to generate more charge carriers, resulting in a significantly decreased resistivity. Overall, these predictions are consistent with the present observations of changes in $R_{MOF}$ flowing Mg<Co<Ni for M-MOF-74.

$NO_2$ Concentration Variations

Figures 7A, 7B:
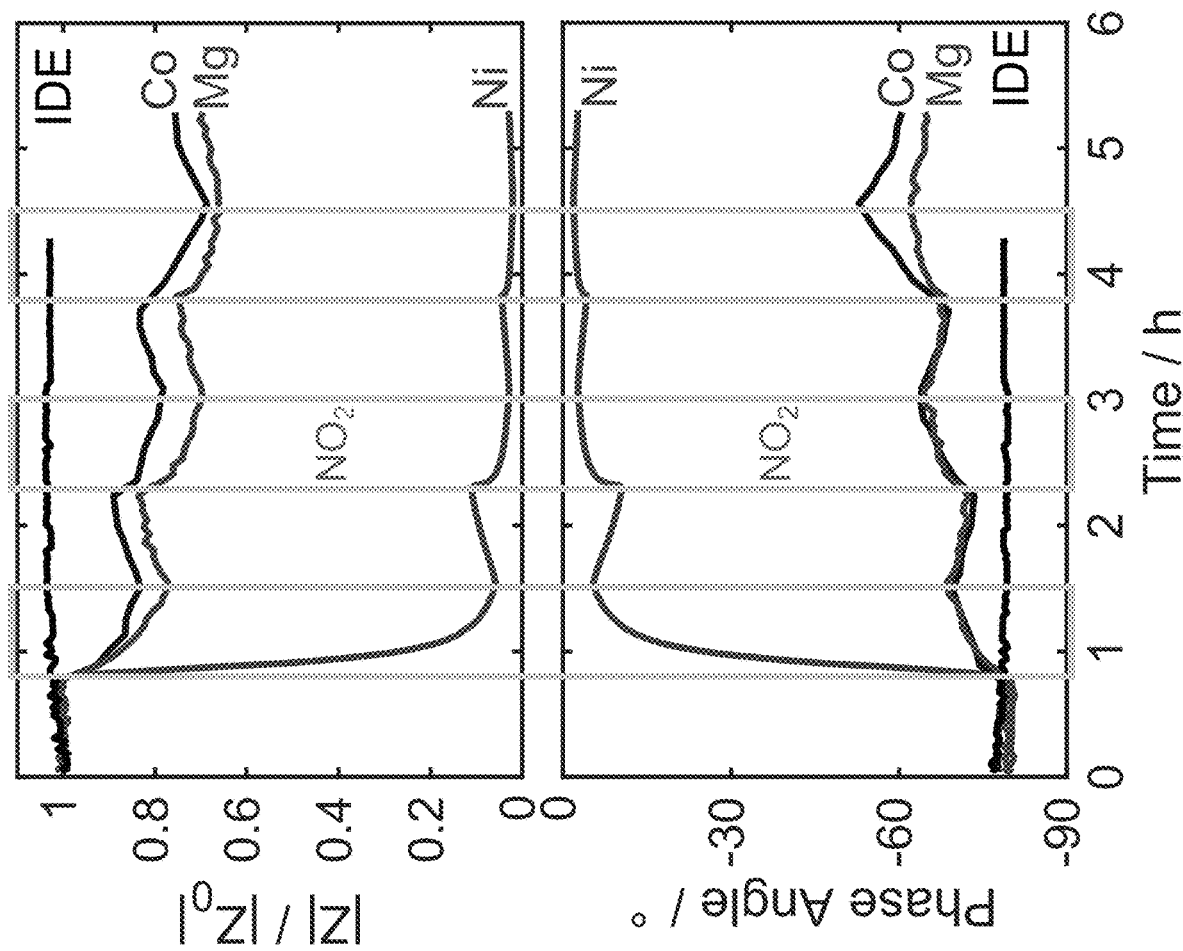
FIGS. 7A and 7B are graphs of normalized impedance magnitude and phase angle, respectively, at 100 mHz for IDEs coated with M-MOF-74 (M=Co, Mg, Ni) compared to a blank IDE during alternating 0.75 h exposures to pure $N_2$ or 5 ppm $NO_2$ at 50° C. $NO_2$ exposure times are highlighted in gray.

To understand how the MOFs respond to varying $NO_2$ concentrations, blank IDEs and IDEs coated in M-MOF-74 (M=Co, Mg, Ni) were activated and exposed to alternating 0.75 h flows of pure $N_2$ or $N_2$ containing trace $NO_2$, while the impedance was constantly measured at 100 mHz. As seen in FIGS. 7A and 7B for 5 ppm $NO_2$, the blank IDE shows no response to pure $N_2$ or 5 ppm $NO_2$, aside from a small increase (<3%) during the first 0.5 h after initial gas flow into the evacuated chamber. As-activated, all MOF-74 variants show no appreciable response to $N_2$ versus vacuum. However, when they are exposed to 5 ppm $NO_2$, the M-MOF-74 coated IDEs reveal a distinct decrease in impedance magnitude (|Z|) and increase in phase angle. Upon removal of $NO_2$, some fraction of the response reverses back towards the initial value, but does not obtain the original, as-activated value.

Figure 5:
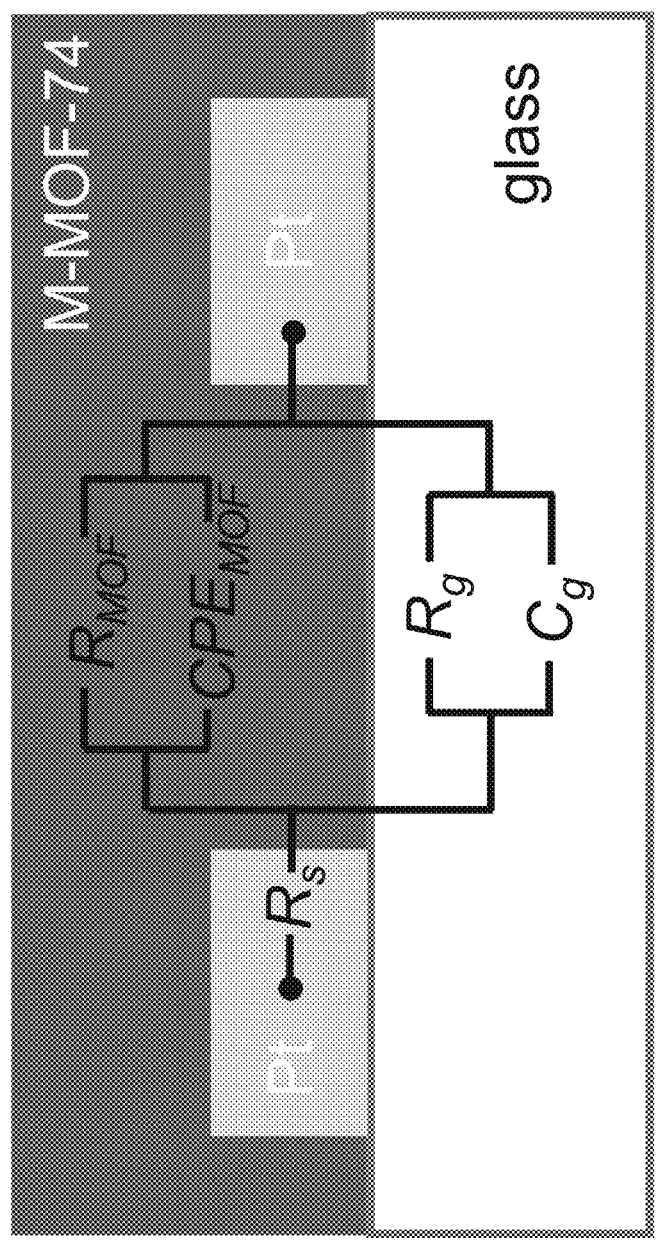
FIG. 5 shows an equivalent circuit used to fit impedance data and extract $R_{MOF}$, the DC resistance of the M-MOF-74 (M=Co, Mg, Ni) film. RS is the series resistance, primarily the Pt leads on the IDE. $R_g$ and $C_g$ are the resistance and capacitance of the IDE/glass substrate. $CPE_{MOF}$ is a constant phase element used to model the MOF's capacitance.
Figure 6:
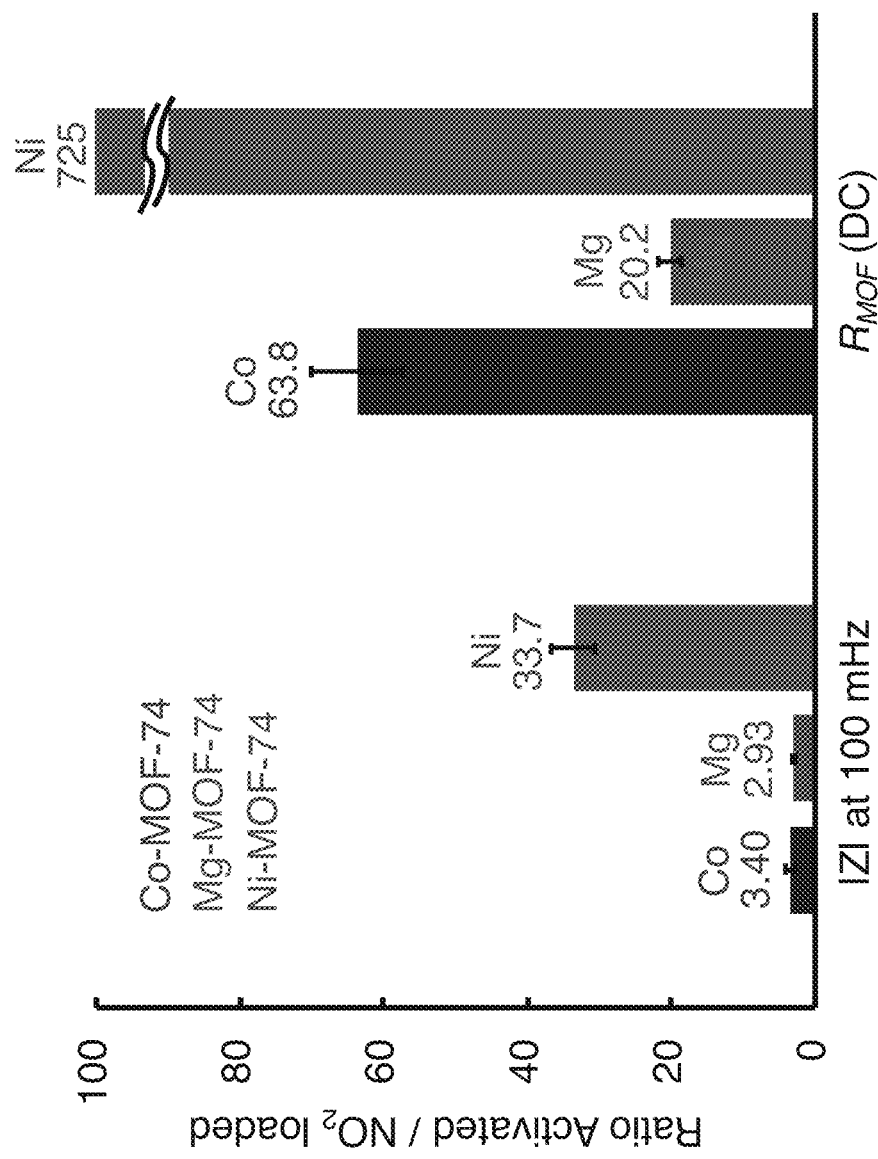
FIG. 6 is a graph showing the ratio of response as-activated to $NO_2$-exposed for (1) impedance magnitude ($|Z_{activated}|/|Z_{NO2}|$) at 100 mHz and (2) MOF DC film resistance ($R_{activated}/R_{NO2}$) for IDEs coated with M-MOF-74 (M=Co, Mg, Ni). $NO_2$ exposure was at 5 ppm $NO_2$ for 8 h at 50° C.
Figure 8A:
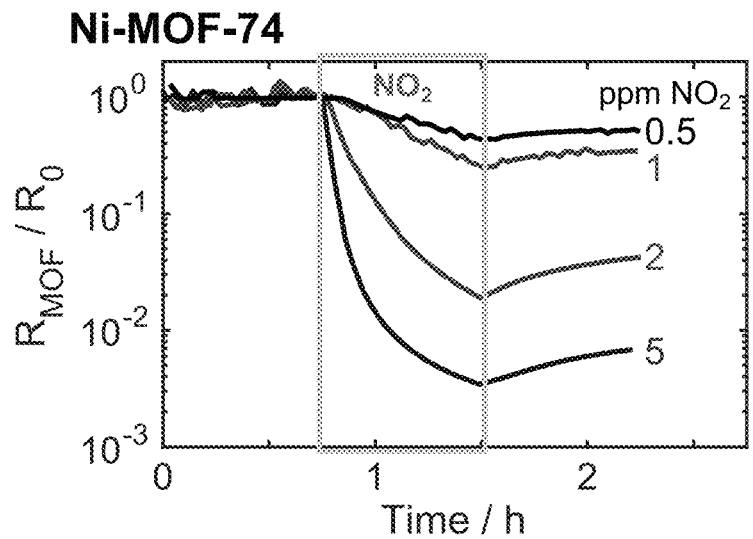
FIGS. 8A, 8B, and 8C are graphs showing MOF-74 film resistance ($R_{MOF}$) in response to variable concentrations of $NO_2$ at 50° C. for 0.75 h.

To extract the MOF resistance ($R_{MOF}$) from these real-time measurements, the full frequency response of each activated sensor was measured prior to and after $NO_2$ exposure and fit to the equivalent circuit shown in FIG. 5. From the continuous measurements at 100 mHz in FIGS. 7A and 7B, it is possible to determine $R_{MOF}$ for each data point. Under this same alternating $NO_2$ flow, the influence of $NO_2$ concentration was investigated at 5, 2, 1, and 0.5 ppm $NO_2$. A typical change in film resistance, $R_{MOF}$, is presented in FIG. 8A for Ni-MOF-74. As expected, $R_{MOF}$ decreases with increasing $NO_2$ concentration. Similar behaviors are seen for Co-MOF-74 and Mg-MOF-74, as summarized in FIG. 8B. As expected, Ni-MOF-74 displayed the largest decrease in $R_{MOF}$ after the 0.75 h exposure. However, Mg-MOF-74 showed a larger decrease than Co-MOF-74 did for 2-5 ppm $NO_2$. This is in contrast to the 8 h exposures (Table 1, FIG. 6), where Co-MOF-74 showed a larger decrease in $R_{MOF}$ than Mg-MOF-74. These differences are attributed to the relative response times. After 0.75 h, Co-, Mg-, and Ni-MOF-74 showed 26%, 55%, and 85% of their respective 8 h changes in $Log(R_{MOF}/R_0)$. Thus, Co-MOF-74 can elicit a larger change in $R_{MOF}$ than Mg-MOF-74 (Table 1), but Co-MOF-74 requires a longer period of exposure to realize this change. The relatively fast response of Mg-MOF-74 compared to Co-MOF-74 is likely influenced by the significantly smaller crystallite size of Mg-MOF-74, making differences in mass transport of $NO_2$ more prominent at short times. While Ni-MOF-74 also shares Co-MOF-74's larger crystallite size, the change in $R_{MOF}$ for Ni-MOF-74 is orders of magnitude larger, making direct comparison more difficult to correlate.

$NO_2$ Sensitivity

Figure 8B:
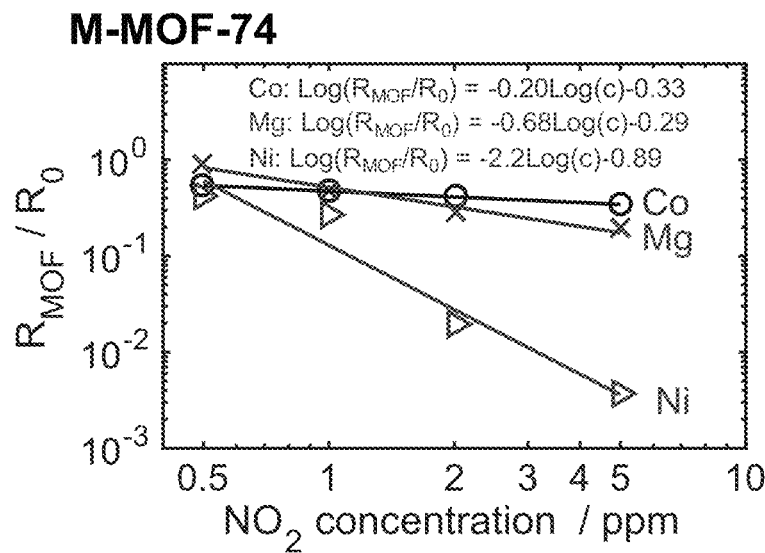

The plot of $R_{MOF}$ vs. $NO_2$ concentration in FIG. 8B is fitted with a typical power-law relation, $R_{MOF}/R_0=Ac^n$, linearized to the form $Log(R_{MOF}/R_0)=n\ Log(c)+B$. Here n and B are constants for a given M-MOF-74, and c is the $NO_2$ concentration in ppm. For all M-MOF-74, n is less than 0, confirming the inverse relation between $R_{MOF}$ and $NO_2$ concentration. For a given M-MOF-74 after 0.75 h, a larger magnitude in n indicates a larger $NO_2$ sensitivity (larger concentration dependence), while a larger magnitude of B signifies a lower limit of detection. Thus, Ni-MOF-74 displayed both the largest $NO_2$ sensitivity and lowest limit of detection. That n does not equal one suggests that the charge carrier mobility and/or concentration are nonlinear functions of $NO_2$ concentration (after 0.75 h). Nevertheless, all sensors displayed good linearity in the 0.5-5 ppm range.

Figure 8C:
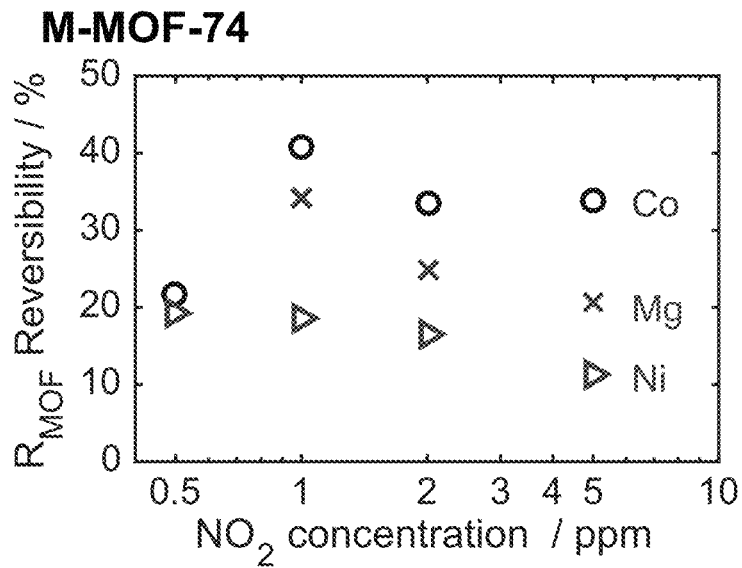

Interestingly, the magnitude of $R_{MOF}$ that decreases after removal of $NO_2$ was found to vary with both M-MOF-74 variant and $NO_2$ concentration, as plotted in FIG. 8C. For all M-MOF-74 variants, the magnitude of the response that reverses back towards the activated value (time=0) decreases with increasing $NO_2$ concentration. This behavior is expected; at higher gas concentrations, more $NO_2$-metal binding sites are occupied, thereby having a smaller concentration of $NO_2$ molecules to release (more chemisorbed versus loosely bound physisorbed). Of the three M-MOF-74 variants, the reversibility in electrical response to 0.75 h of 0.5-5 ppm $NO_2$ was ordered Co>Mg>Ni, consistent with the relative bonding strengths of the M-MOF-74 variants with $NO_2$ (i.e., higher bonding strengths show lower reversibility). See K. Tan et al., *Chem. Mater.* 29, 4227 (2017). Co-MOF-74 showed the most reversible change in $R_{MOF}$, with up to one third of the change in $R_{MOF}$ recoverable after 0.75 h at 1 ppm $NO_2$. On the other hand, Ni-MOF-74 displayed the least reversible response upon removal of $NO_2$. This large, irreversible response makes Ni-MOF-74 ideal for dosimeter or integrating sensor applications.

Ni-MOF-74: $NO_2$ Selectivity

Figure 9A:
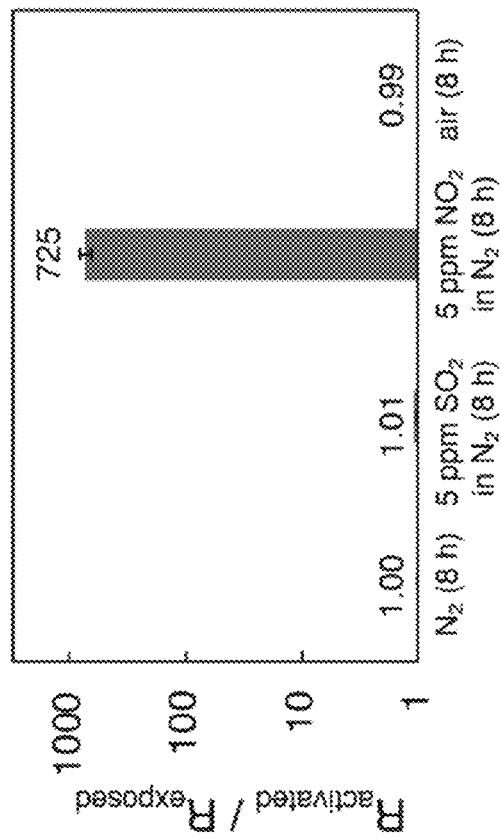
FIGS. 9A and 9B are graphs of the ratio of Ni-MOF-74 resistance ($R_{MOF}$) as-activated to exposed to different environments at 50° C., demonstrating a highly selective response toward $NO_2$.

It is important to understand how other relevant gases might interact with Ni-MOF-74 during $NO_2$ detection. $H_2O$ and $CO_2$, present in ambient atmosphere, are known to be adsorbed by M-MOF-74. These gases and $SO_2$, also adsorbed by M-MOF-74, are often present in environments containing industrial flue gases. To identify if these gases would interfere with Ni-MOF-74's strong response to $NO_2$, Ni-MOF-74 was activated and exposed to 5 ppm $SO_2$ in $N_2$, and ambient air (25° C., 50% RH, 400 pm $CO_2$) heated to 50° C. The results of these experiments are plotted in FIG. 9A and compared to previous exposures to 5 ppm $NO_2$ in $N_2$.

After 8 h exposure to pure $N_2$, 5 ppm $SO_2$ in $N_2$, or air, no appreciable change in Ni-MOF-74 resistance ($R_{MOF}$) was observed, as compared to a 725× decrease in $R_{MOF}$ for 5 ppm $NO_2$ in $N_2$. This demonstrates the excellent electrical selectivity of Ni-MOF-74 to $NO_2$.

Figure 9B:
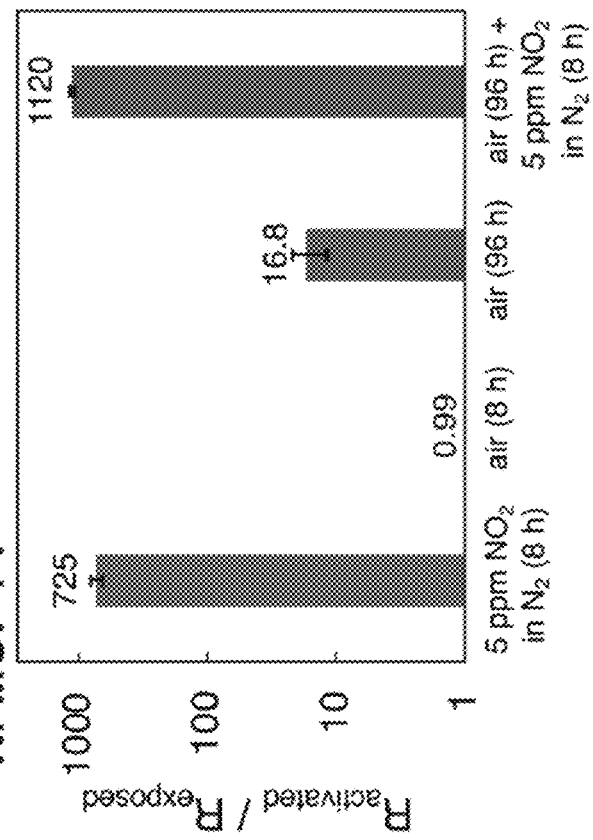

It was unexpected that no change in $R_{MOF}$ was observed in air after 8 h, for as-cast sensors left on the lab bench unactivated typically increase ≈10× in $R_{MOF}$ upon activation. Therefore, an extended 96 h air exposure was performed for Ni-MOF-74, resulting in a decrease in $R_{MOF}$ of 16.8×. Directly thereafter, these sensors were exposed to 5 ppm $NO_2$ in $N_2$, showing a 66.5× further decrease in $R_{MOF}$, as compared in FIG. 9B. Despite air exposure, Ni-MOF-74's rapid response to $NO_2$ was preserved; a >2× change in $R_{MOF}$ was detectable after only 2 min of $NO_2$ exposure. Overall, it is concluded that any $H_2O$ or $CO_2$ slowly adsorbed from the air did not interfere with the Ni-MOF-74 sensor's ability to rapidly respond to $NO_2$. The overall response for the air+$NO_2$ exposed samples (66.5×16.8=1120×) is larger than that of Ni-MOF-74 only exposed to $NO_2$ (725×) and may represent a synergistic interaction between $H_2O$ and $NO_2$ for electrical conduction in Ni-MOF-74. Nevertheless, Ni-MOF-74 shows promising selectivity in electrical response to $NO_2$ over $N_2$, $SO_2$, and air–$CO_2$, $H_2O$.

The source of this selective electrical response is believed to be related to the relative electronic structures of the Ni-MOF-74 and the competing gas species. While many different gas molecules will readily adsorb to the unsaturated metal sites in Ni-MOF-74, a large change in $R_{MOF}$ is only expected if there is a significant amount of MOF-adsorbate electron transfer, creating new unoccupied electron states that facilitate charge transport in Ni-MOF-74. Thus, adsorption of triply bound $N_2$, with its tightly held electrons, is not expected to influence $R_{MOF}$.

On the other hand, $NO_2$ is a radical molecule that can serve as both an electron acceptor and donor. The $NO_2$ highest occupied molecular orbital (HOMO) and lowest unoccupied molecular orbital (LUMO) sits below the Ni-MOF-74's HOMO, which contains significant contributions from Ni electrons. See K. Tan et al., *Chem. Mater.* 29, 4227 (2017); L. Sun et al., *Chem Sci.* 8, 4450 (2017); and J. A. Rodriquez et al., *J. Mol. Catal. A: Chem.* 167, 47 (2001). As discussed previously, electrons from the Ni-MOF-74 HOMO may be transferred to the $NO_2$ LUMO, creating newly reorganized unoccupied states in Ni-MOF-74, facilitating electronic transport, and decreasing $R_{MOF}$.

Compared to $NO_2$, $SO_2$ displays a LUMO at energy levels much closer to vacuum level. See K. Tan et al., *Chem. Mater.* 29, 4227 (2017); and J. A. Rodriquez et al., *J. Mol. Catal. A: Chem.* 167, 47 (2001). This significantly impedes electron transfer; reports have suggested that $SO_2$ adsorption in M-MOF-74 is more akin to physisorption than chemisorption. See K. Tan et al., *Chem. Mater.* 29, 4227 (2017). Therefore, no significant change in $R_{MOF}$ is expected upon adsorption of $SO_2$.

Likewise, significant charge transfer is not expected for $CO_2$ due to relative band locations. Moreover, studies on the competitive adsorption of $CO_2$ and $H_2O$ suggest that $CO_2$ is preferentially exchanged for $H_2O$, making significant adsorption of $CO_2$ from air unlikely in this study.

Interactions with $H_2O$ are more complex. The LUMO of water sits above Ni-MOF-74's HOMO; significant electron transfer is not expected, consistent with reports of molecularly adsorbed $H_2O$, and no dissociation. Nevertheless, high binding energy of $H_2O$, only slightly less than that of $NO_2$, indicates a strong interaction with the metal center. See K. Tan et al., *Chem. Mater.* 27, 2203 (2015). Calculations have predicted that the decreased electron density on a Zn-MOF-74 metal center leads to an ≈30× decrease in effective mass for Zn-MOF-74 electrons. See P. Canepa et al., *J. Mater. Chem. A* 3, 986 (2015). As effective mass is theoretically proportional to resistivity, a similar decrease in $R_{MOF}$ is expected, on par with the 16.8× decrease in $R_{MOF}$ we observe for Ni-MOF-74 in air.

Example: MOF-Based Sensor Via Functionalization of IDE/Glass Substrates

The nature of the dropcast films in the MOF-based sensor described above can inherently lead to random contacts between the electrode surface and the MOF material. Therefore, the ability to grow dense MOF films onto an IDE where the MOF crystal interface is covalently bound may lead to more sensitive detection of $NO_2$. To alleviate the random interfacial contacts between the sensing MOF material and the electrode surface, the material can be grown directly onto the sensor surface as a thin continuous film, akin to a selective nanoporous membrane. The selective nature of the continuous membrane-like thin film will allow the desired analyte to enter the MOF pores and interact with the sensing electrodes while blocking unwanted chemical species. The thin film MOF may also impart a faster detection response for the sensor due to fast diffusion of the analyte through the thinner film.

Many methods exist to make a MOF thin film, including layer-by-layer deposition, electrochemical, and direct synthesis. See A. Bétard and R. A. Fischer, *Chem. Rev.* 112, 1055 (2012); O. Shekhah et al., *Chem. Soc. Rev.* 40, 1081 (2011); D. Zacher et al., *Chem. Soc. Rev.* 38, 1418 (2009); E. D. Spoerke et al., *J. Phys. Chem. C* 121, 4816 (2017); U. Mueller et al., *J. Mater. Chem.* 16, 626 (2006); and Y. Liu et al., *Microporous Mesoporous Mater.* 118, 296 (2009).

Directly growing the MOF onto the electrode surface would impart the most intimate contact between the MOF and the electrode surface. However, there are a number of pitfalls possible to direct growth methods of MOFs on to the surface, such as little to no crystal growth on the surface (just bulk solution crystal growth), a discontinuous film on the surface, or poor adhesion of the resulting crystals. Growing a continuous, strongly adhering MOF film onto the sensor surface is not an easy feat and requires surface functionalization in order to facilitate the nucleation and growth of the MOF crystals which can be covalently bound to the surface. There are several demonstrated methods for functionalizing electrode surfaces (metal or glass) including silanes, thiols, and diazonium. See A. Bétard and R. A. Fischer, *Chem. Rev.* 112, 1055 (2012); A. Huang et al., *Angew. Chem., Int. Ed.* 49, 4958 (2010); D. Zacher et al., *J. Mater. Chem.* 17, 2785 (2007); D. Zacher et al., *Chem. Soc. Rev.* 38, 1418 (2009); M. T. Conato and A. J. Jacobson, *Microporous Mesoporous Mater.* 175, 107 (2013); L. J. Small et al., *Langmuir* 30, 14212 (2014); L. J. Small et al., *Nanoscale* 7, 16909 (2015); and C. Saby et al., *Langmuir* 13, 6805 (1997). Previously, demonstrations of MOF films have shown to be more uniform when grown on a metal ion precursor "seeded" layer of surface thiols on gold surfaces functionalized with carboxylates that have metal ions covalently bound to the functional groups before the MOF growth step occurs. See M. T. Conato and A. J. Jacobson, *Microporous Mesoporous Mater.* 175, 107 (2013). Regardless of the functionalization type, the functional group presented on the end of the surface functionalization molecule will directly impact the growth of the MOFs, where typically carboxylate functional groups are desired.

As an example of the invention, imperfect but continuous and overlapping crystallite thin films of M-MOF-74 (M=Co, Mg, Ni) were grown on functionalized IDE/glass substrates. The IDE response largely depends on what is located between the Pt sensing electrodes (as long as there is good contact between the electrodes and the sensing material). As such, the glass surface, located between the interdigitated electrodes, was targeted with surface modification to enable the growth the MOF material. First, the glass surface of the substrate was functionalized using an amine terminated silane layer that bonds to the glass. The amine on the silane was then converted to a carboxylic acid functional group through a selective anhydride conversion step which creates a suitable surface for the MOF crystals to nucleate and grow. This functionalization allows a largely uniform growth of the MOF, forming a gas selective nanoporous thin film over the entire surface of the substrate, including the unfunctionalized platinum electrodes. By growing a thin film MOF on the IDE/glass, the detection of $NO_2$ through monitoring the electrical impedance of the IDE becomes more sensitive and faster than a dropcast film of bulk MOF powder.

Sensor Fabrication

As with the dropcast sensors, platinum IDEs on glass substrates were obtained from DropSens (product G-ID-EPT10) and used as received. These IDEs contain 125 pairs of platinum lines 250 nm thick and 10 µm wide with a spacing of 10 µm between lines.

Figure 10:
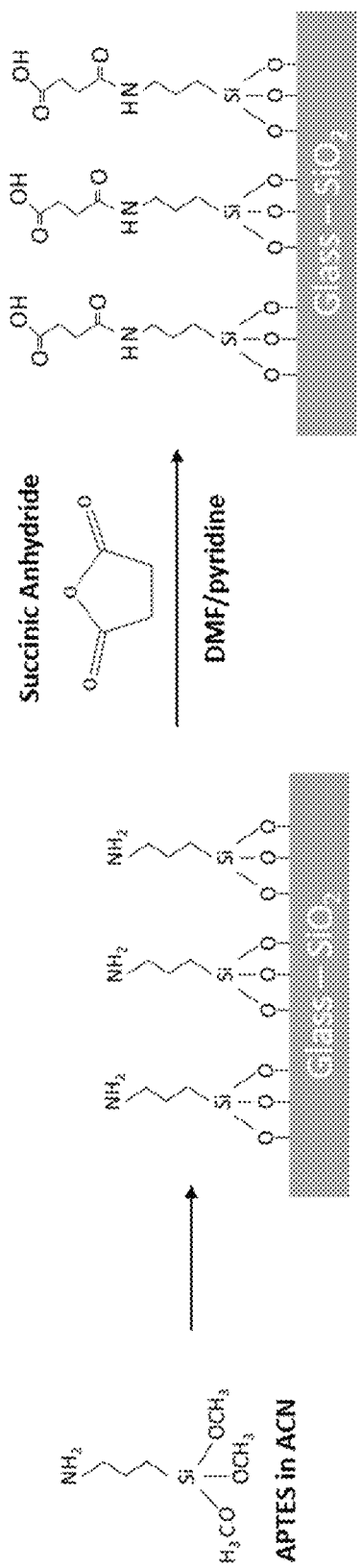
FIG. 10 is schematic illustration of a surface functionalization of a glass substrate by reaction of an amino silane (APTES) yielding a layer of amine terminated functional groups followed by reaction with succinic anhydride to convert the amine termination into a carboxylic acid functional group.

Functionalization of IDEs was achieved by a two-step process, depicted in FIG. 10. First, the IDE/glass substrate was fully immersed in 5 vol % (4-aminopropyl)triethoxysilane (APTES; 0.25 mL) in acetonitrile (5 mL) for 1 h. The substrate was then rinsed in acetonitrile and dried under $N_2$ flow to provide an amine-functionalized surface. Next, the amine-functionalized substrates were immersed in 0.1 M succinic anhydride (50 mg) in N,N'-dimethylformamide (DMF, 4.95 mL) with 1 vol % anhydrous pyridine (50 µL) in a sealed vial for 24 h. The surface-bound amine group attacks the succinic anhydride, performing a ring opening on the anhydride and converting the amine to a carboxylate-terminated functional group. As this functionalization is completed at room temperature, the functional group remains as a carboxylic acid and is not anticipated to ring close back into succinimide. The substrates were then rinsed with DMF and dried under $N_2$ flow.

To grow a Co-MOF-74 thin film on the functionalized surface, cobalt acetate tetrahydrate (0.063 g, 0.253 mmol) and 2,5-dihydroxyterephthalic acid (0.025 g, 0.126 mmol) were dissolved with sonication in DMF (3.5 mL), water (3.5 mL) and ethanol (3.5 mL) in a 15 mL Teflon-lined steel autoclave. The functionalized substrate was added and then heated at 105° C. for 48 h.

To grow a Mg-MOF-74 thin film on the functionalized surface, Mg-MOF-74 was synthesized in a similar method as previously described. See L. Taek and M. W. Shin, *Surf. Interfaces* 22, 100845 (2021). Magnesium nitrate hexahydrate (0.095 g, 0.370 mmol) and 2,5-dihydroxyterephthalic acid (0.022 g, 0.111 mmol) were dissolved with sonication in DMF (9 mL), water (0.6 mL) and ethanol (0.6 mL) in a 20 mL borosilicate glass vial. The functionalized substrate was added and then heated at 125° C. for 48 h.

To grow a Ni-MOF-74 thin film on the functionalized surface, nickel acetate tetrahydrate (0.075 g, 0.301 mmol) and 2,5-dihydroxyterephthalic acid (0.025 g, 0.126 mmol) were dissolved with sonication in DMF (3.5 mL), water (3.5 mL) and ethanol (3.5 mL) in a 15 mL Teflon-lined steel autoclave. The functionalized substrate was added and then heated at 105° C. for 48 h.

All MOF thin films grown on IDE/glass substrates were solvent exchanged in acetone for 72 h prior to any electrochemical testing and allowed to dry in air for 30 minutes before use.

Characterization of MOF Thin Films

Figure 11A:
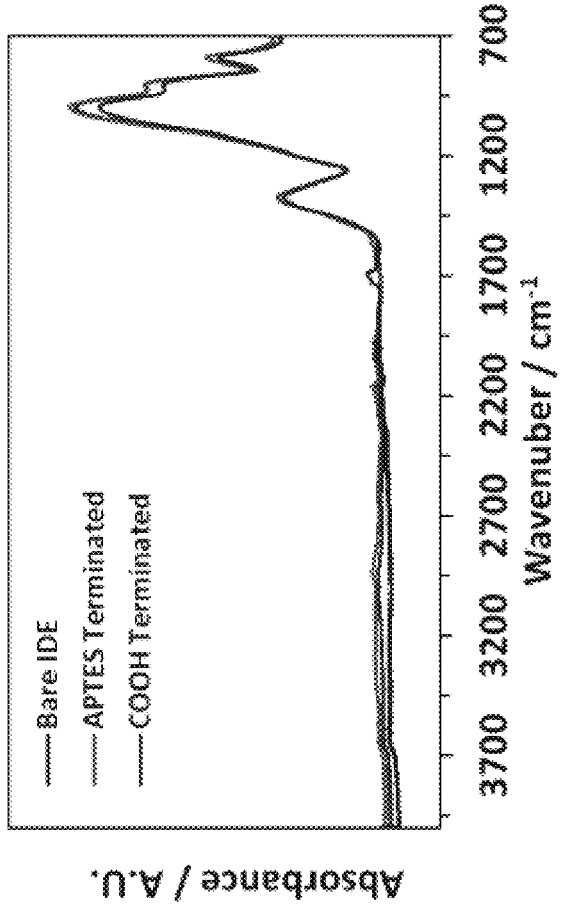
FIGS. 11A and 11B show infrared spectra for the bare IDE, IDE after silane functionalization, IDE after succinic anhydride functionalization.
Figure 11B:
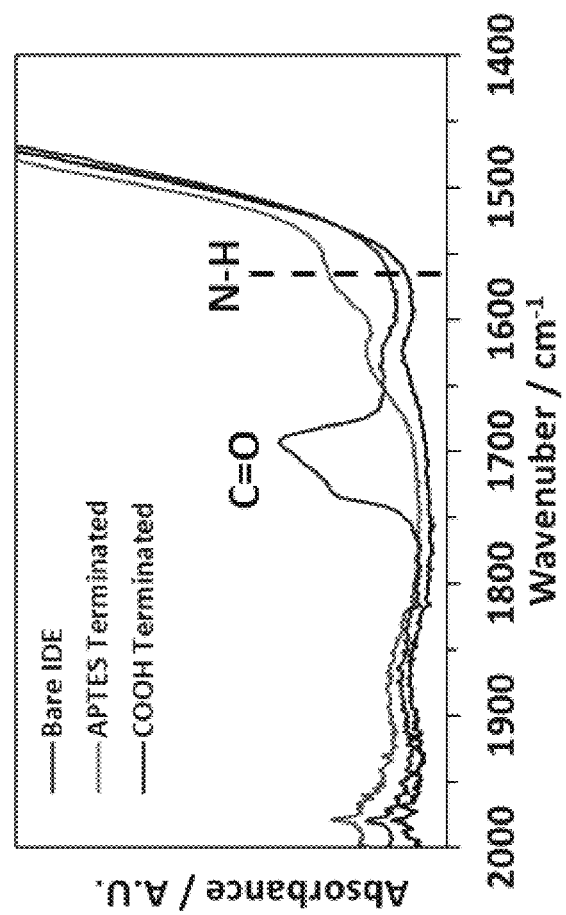

To ascertain the extent of functionalization of the IDEs post-silane and post-COOH steps, infrared spectroscopy (IR) was undertaken, and the results are shown in FIGS. 11A and 11B. Post-silane treatment, the successful formation of an amine-terminated surface was confirmed by the peak near 1560 $cm^{-1}$ (FIG. 11B), associated with the N—H bend of a primary amine. Upon treatment with succinic anhydride to form a COOH-terminated surface, a carbonyl peak near 1690 $cm^{-1}$ appeared, while the N—H peak disappeared. Disappearance of this N—H peak at 1560 $cm^{-1}$ is consistent with the conversion of a primary amine to a secondary amine as seen in FIG. 10. Likewise, the appearance of the C=O peak near 1690 $cm^{-1}$ is consistent with the formation of amide and COOH groups. Thus, it is concluded that this two-step process has successfully functionalized the glass substrate with carboxylate groups.

Figure 12:
FIG. 12 are photographs of the bare IDE with no MOF growth, and IDEs with Co-MOF-74, Mg-MOF-74, and Ni-MOF-74 thin film. IDEs are 22.8×7.6 mm.

This type of surface functionalization, specifically —COOH termination, has been used in the literature previously to grow thin film layers of MOFs. See O. Shekhah et al., *Chem. Soc. Rev.* 40, 1081 (2011); and D. Bradshaw, *Chem. Soc. Rev.* 21, 2344 (2012). As described above, M-MOF-74 (M=Co, Mg, Ni) thin films were synthesized on carboxy-functionalized IDEs from a solvothermal synthesis at 105° C. for Ni- and Co-MOF-74, and 125° C. for Mg-MOF-74. See L. Taek and M. W. Shin, *Surf. Interfaces* 22, 100845 (2021). Representative photographs of these IDEs with M-MOF-74 thin films are shown in FIG. 12. Both Co- and Ni-MOF-74 thin films appeared as a uniform transparent film across the IDE; regions near the IDE bottom were mechanically removed to enable electrical contact. Mg-MOF-74, on the other hand, appeared as a bright yellow film. It should be noted that without surface functionalization, MOF failed to grow on the IDEs.

Figure 13:
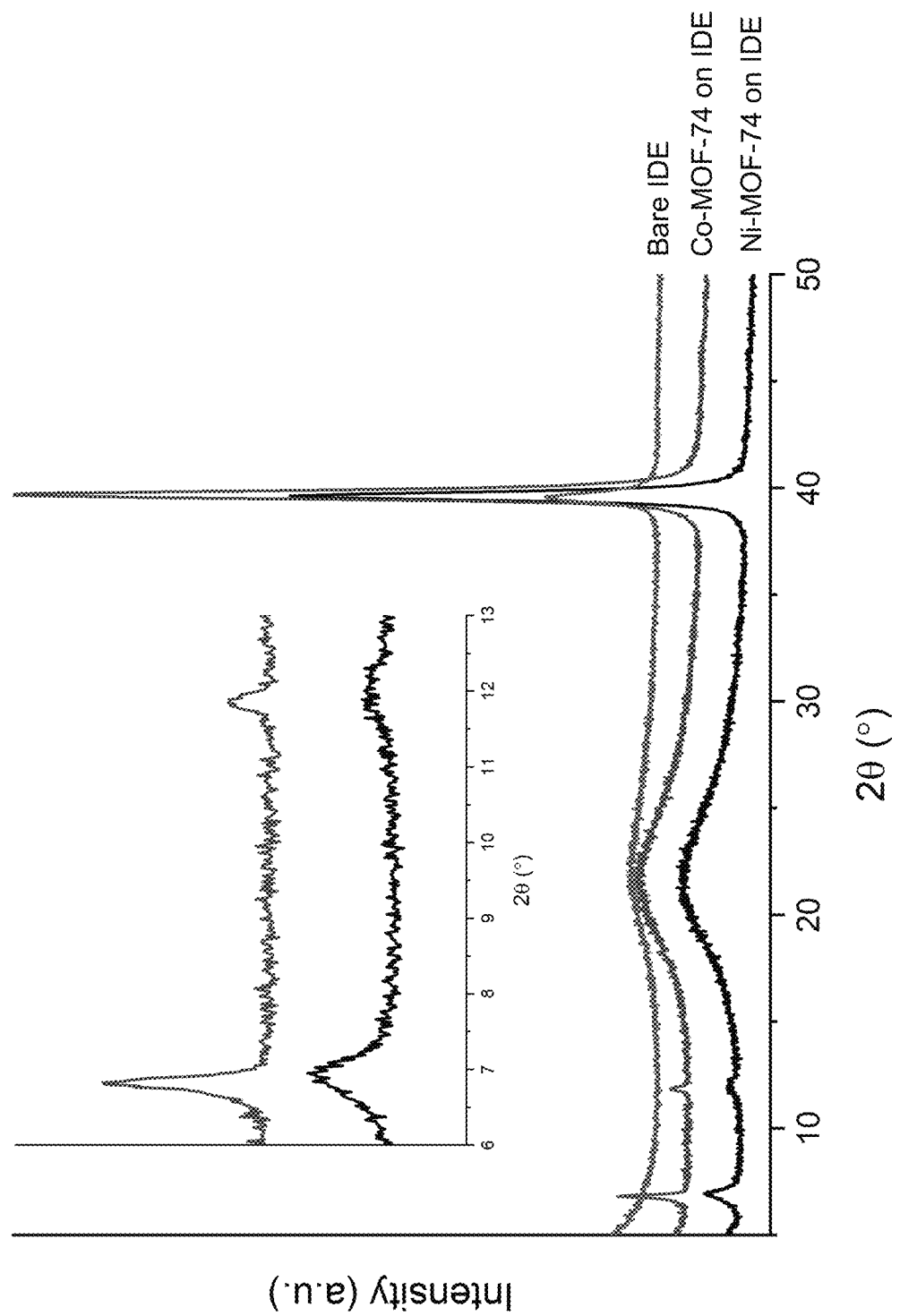
FIG. 13 shows powder X-ray diffraction patterns for bare IDE (blue), Co-MOF-74 and Ni-MOF-74 grown on IDE/glass substrates. Inset from 6 to 13° 2θ highlights the 2 main MOF peaks for each. The peak at 40° 2θ corresponds to Pt, and the broad diffuse hump at 15-30° 2θ corresponds to glass.
Figure 14:
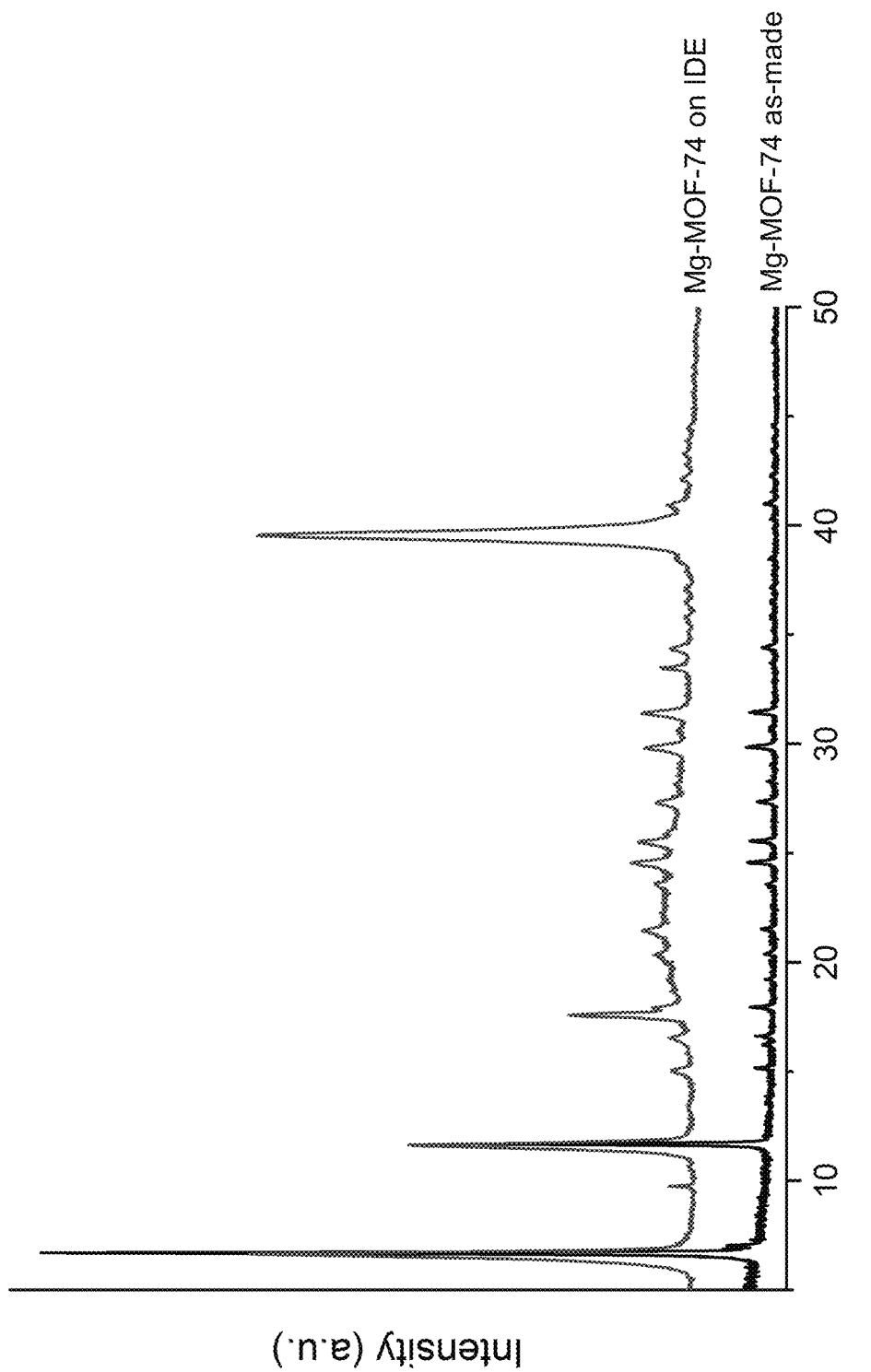
FIG. 14 shows powder X-ray diffraction patterns for bulk Mg-MOF-74 and the Mg-MOF-74 grown on IDE/glass substrates. The peak at 40° 2θ corresponds to Pt, and the broad diffuse hump at 15-30° 2θ corresponds to glass. The peak at 17.5° 2θ corresponds to DOBDC linker, that is later washed out with water.

To ensure the thin film growth was of the desired MOF, PXRD was used to confirm phase purity and crystallinity. Powder XRD data collected on the bare IDE with no MOF growth as a comparison with those IDEs with MOF thin film growth (shown in FIG. 13). The PXRD patterns of each thin film highlighted the two primary MOF peaks at 6.8 and 11.6° 2θ. The patterns also showed a broad amorphous hump at 14-30° 2θ corresponding to the glass substrate, and a sharp peak near 40° 2θ corresponding to the platinum electrodes. Due to the increased thickness of the Mg-MOF-74 thin film (FIG. 14) compared to the Co- and Ni-MOF-74 thin films (FIG. 13), more Bragg peaks relating to the MOF at higher angle can be seen, with less of the amorphous glass present. The PXRD pattern for bulk Mg-MOF-74 is shown in FIG. 14 as an archetypal MOF, because all members of the MOF-74 family are isostructural.

Figure 15:
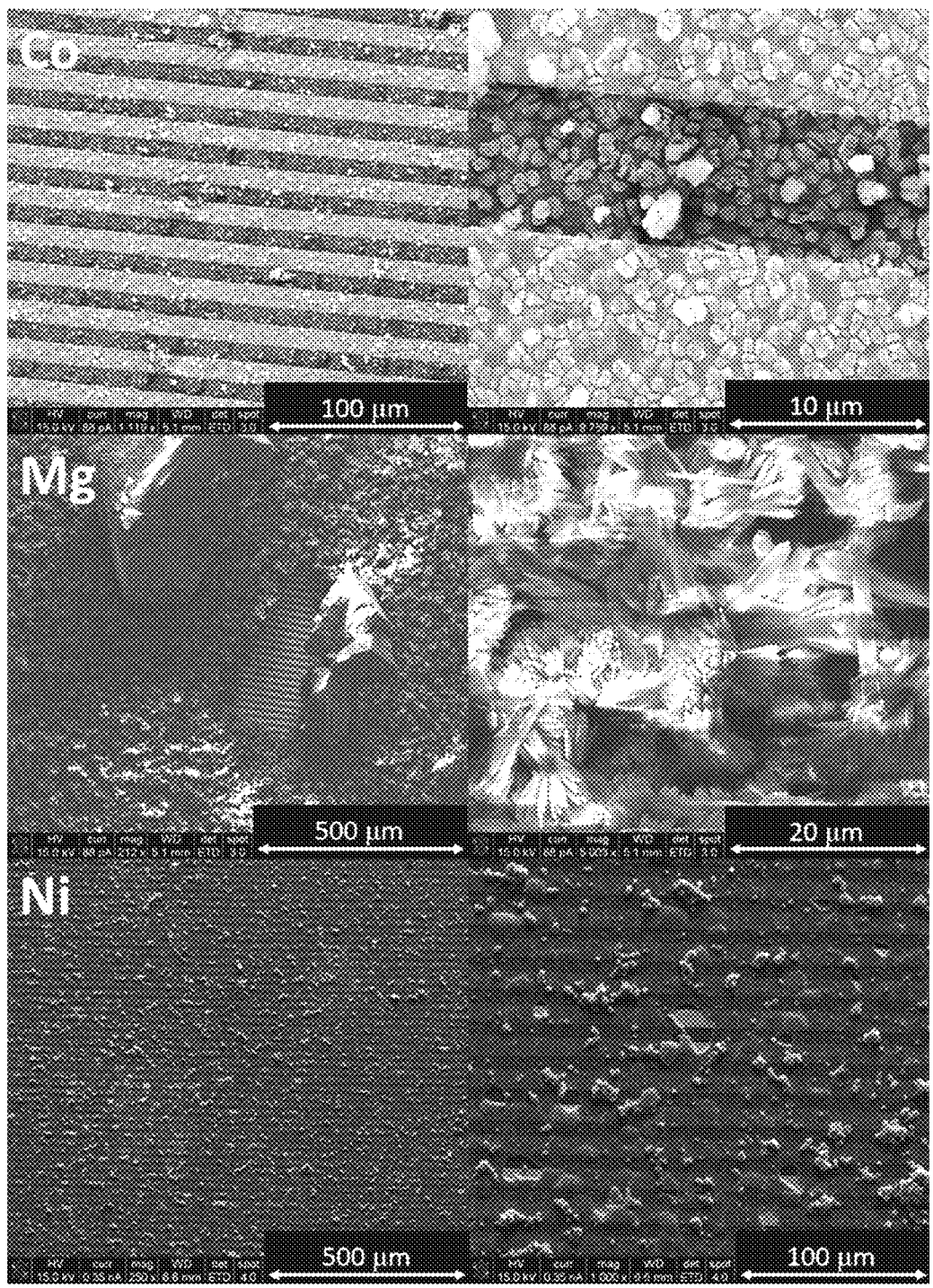
FIG. 15 shows scanning electron micrographs of Co-MOF-74 (top), Mg-MOF-74 (middle) and Ni-MOF-74 (bottom) thin films grown on silica/Pt functionalized IDEs.

To corroborate what could be seen by eye, SEM of each MOF thin film was undertaken to ascertain MOF coverage all over the IDE/silica surface in a continuous fashion. Characteristic SEM micrographs are presented in FIG. 15. Each MOF boasted a thin continuous crystalline film, with the thickness of the thin films increasing from Co<Ni<Mg. The Co-MOF-74 grown on the IDE had the thinnest film and the film was made of very small polycrystallites, resulting in some areas with no crystal growth. Both Mg-MOF-74 and Ni-MOF-74 boasted consistent sizes of polycrystallites. The crystallites for the Mg-MOF-74 thin film had grown as small aggregated single crystals with a flower-type morphology. However, some of the MOF crystals had grown much larger than others, creating an uneven surface (FIG. 15). This size of crystallites allowed for stacking on top of each other and therefore for a thicker film to grow. However, this is not advantageous as the thicker film was much more susceptible to chipping and cracking due to stress, as can be seen by in both FIG. 12 and FIG. 15. The Mg-MOF-74 sample was gold sputter coated twice; however it was still highly susceptible to charging at higher magnifications.

Figure 16:
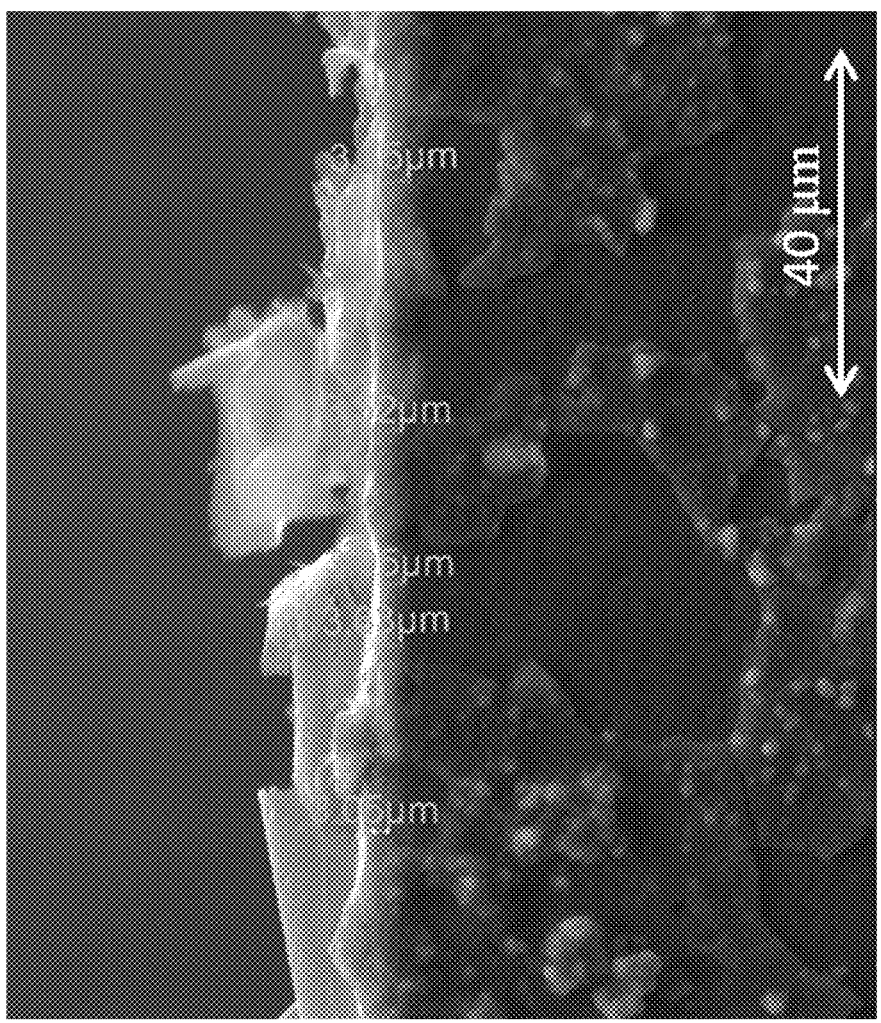
FIG. 16 shows SEM of the Ni-MOF-74 thin films as a cross section. Thickness of the thin films is highlighted by green text.

Furthermore, the cross-section of the Ni-MOF-74 IDE was imaged and showed a continuous thin film MOF layer on the glass surface, as shown in FIG. 16. The homogenous MOF thin film was shown to have a similar thickness of ca. 3.40 μm all along the IDE. It is clear to see that the film is not perfect; the surface is rough and there are defects. However, the film is continuous and the overlapping of polycrystallites allows for contact with the IDE Pt electrodes and fully spans the glass surface active area between the Pt electrodes. Therefore, the use of these thin films as a sensor for $NO_2$ does not require them to be defect-free, but solely continuous and overlapping growth.

Electrochemical Detection of $NO_2$

As an example, the Ni-MOF-74 was further investigated for its use as a $NO_2$ adsorbent and as a direct electrical sensor under $NO_2$ exposure. The Ni-MOF-74 thin film sensor was compared to a sensor utilizing a dropcast Ni-MOF-74 film (made using bulk synthesized MOF powder). The sensors were separately placed in a custom-built adsorption chamber and first activated at 200° C. under vacuum as described above. Degradation of the MOF is not of concern since these MOFs are known to be stable up to 400° C. See D. Cattaneo et al., *RSC Adv.* 6, 14059 (2016). This activation was performed to remove both coordinated solvent molecules and solvent remaining in the pores of the MOF after synthesis. After activation, the sensors were equilibrated to 50° C. under 500 sccm $N_2$ at ambient pressure. A stable impedance response at 100 mHz was verified over 0.75 h, at which time 5 ppm $NO_2$ in $N_2$ was introduced to the chamber.

After introduction of $NO_2$ the impedance of the thin film sensor quickly decreases in an exponential fashion, as shown in FIGS. 17A and 17B. The impedance magnitude (|Z|) began at 22.7 GΩ, dropping to 11.3 GΩ within 5 minutes, and 0.184 GΩ in 4 h. Likewise, the phase angle started at −77.5°, increasing to −38.7° within 5 minutes and −0.796° in 4 h. These data clearly show that the thin film MOF quickly transitioned from a capacitive to resistive response with a 123× decrease in impedance magnitude upon exposure to $NO_2$.

By comparison, the sensor made with a dropcast film of bulk MOF powder also decreased upon exposure to the $NO_2$. However, the rate and magnitude of change of the dropcast sensor were both smaller than the thin film sensor. Here the impedance magnitude decreased from 25.0 to 22.2 GΩ in 5 minutes, and down to 1.79 GΩ in 4 hours. Similarly, the phase angle increased from −79.2° to −74.2° in 5 minutes and −5.96° in 4 h.

The observed response to $NO_2$ shows that the sensor made with the Ni-MOF-74 MOF thin film has a faster response to $NO_2$ than bulk Ni-MOF-74 powder sensor. Therefore, these Ni-MOF-74 thin film sensors can be useful in applications where fast response time is a requirement. The use of a thin film enables this fast response time as compared to the thicker films of dropcast bulk MOF. As the Ni-MOF-74 resistance is influenced by the weight % of $NO_2$ adsorbed, thinner films will require fewer moles of $NO_2$ to show the same change in impedance.

The present invention has been described as low power sensor for $NO_2$ detection. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A low power nitrogen oxide sensor, comprising:
   an electrically insulating substrate;
   a pair interdigitated electrodes disposed on the substrate;
   a nitrogen-oxide-capture film disposed on the pair of interdigitated electrodes and the substrate; and
   a frequency response analyzer configured to measure the impedance response of the nitrogen-oxide-capture film when nitrogen oxide is absorbed in the nitrogen-oxide-capture film and an alternating voltage is applied to the pair of interdigitated electrodes.

2. The sensor of claim 1, wherein the nitrogen-oxide-capture film comprises a metal organic-framework (MOF) material.

3. The sensor of claim 2, wherein the MOF material comprises M-MOF-74, wherein M is a metal.

4. The sensor of claim 3, wherein the metal is cobalt, magnesium, or nickel.

5. The sensor of claim 2, wherein the MOF material comprises RE-DOBDC, where RE is a rare-earth element and DOBDC is dihydroxyterephthalic acid.

6. The sensor of claim 1, wherein the nitrogen-oxide-capture film comprises a zeolite material.

7. The sensor of claim 6, wherein the zeolite material comprises an SSZ-13 or SAPO zeolite.

8. The sensor of claim 1, wherein the nitrogen-oxide-capture film has a thickness of less than 100 μm.

9. The sensor of claim 8, wherein the nitrogen-oxide-capture film has a thickness of less than 10 μm.

10. The sensor of claim 1, wherein the nitrogen-oxide-capture film is dropcast deposited on the pair of interdigitated electrodes and the substrate.

11. The sensor of claim 1, wherein the nitrogen-oxide-capture film comprises a continuous MOF thin film grown from a functionalized surface of the substrate.

12. The sensor of claim 11, wherein the functionalized surface comprises a carboxylate functionalized surface.

13. The sensor of claim 1, wherein the substrate comprises a silica glass substrate.

14. The sensor of claim 1, wherein the alternating voltage has a frequency between 1 mHz and 1 MHz.

15. The sensor of claim 14, wherein the frequency corresponds to a RC transition frequency that leverages the capacitive component of the MOF to increase the signal strength while still enabling the larger signal change associated with the DC resistance to be calculated.

16. The sensor of claim 1, further comprising a high impedance interface connected in series with the frequency response analyzer.

17. The sensor of claim 1, wherein the sensor dissipates less than 10 nW when operating.

18. The sensor of claim 17, wherein the sensor dissipates less than 15 pW when operating.

19. The sensor of claim 1, wherein the sensor has a $NO_2$ detection limit of less than 0.5 ppm.

20. The sensor of claim 1, wherein an operating temperature of the sensor is less than 75° C.

21. The sensor of claim 1, wherein the nitrogen oxide comprises $NO_2$.

22. A method for fabricating a low power nitrogen oxide sensor, comprising;
   providing a pair of interdigitated electrodes on a surface of a substrate,
   functionalizing the surface of the substrate, and
   growing a continuous MOF thin film from the functionalized surface.

23. The method of claim 22, wherein the substrate comprises a silica glass and the functionalizing step comprises:
   immersing the substrate in an acetonitrile solution comprising an aminosilane, to produce an amine-terminated surface on the substrate,
   immersing the amine-terminated surface in a solution comprising succinic anhydride, thereby converting the amine to a carboxylic acid terminated group and producing a carboxylate functionalized surface on the substrate.

24. The method of claim 23, wherein the aminosilane comprises 4-aminopropyl)triethoxysilane.

25. The method of claim 22, wherein the MOF thin film comprises a M-MOF-74, wherein M is a metal.

* * * * *